(12) United States Patent
Imai

(10) Patent No.: US 10,672,123 B2
(45) Date of Patent: Jun. 2, 2020

(54) IMAGE PROCESSING APPARATUS, ENDOSCOPE SYSTEM, AND IMAGE PROCESSING METHOD

(71) Applicant: FUJIFILM Corporation, Tokyo (JP)

(72) Inventor: Yoshiro Imai, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 212 days.

(21) Appl. No.: 15/928,102

(22) Filed: Mar. 22, 2018

(65) Prior Publication Data

US 2018/0211385 A1 Jul. 26, 2018

Related U.S. Application Data

(63) Continuation of application No. PCT/JP2016/078539, filed on Sep. 27, 2016.

(30) Foreign Application Priority Data

Sep. 28, 2015 (JP) .................................. 2015-189872

(51) Int. Cl.
*G06K 9/00* (2006.01)
*G06T 7/00* (2017.01)
(Continued)

(52) U.S. Cl.
CPC .............. *G06T 7/0012* (2013.01); *A61B 1/00* (2013.01); *A61B 1/04* (2013.01); *A61B 5/0261* (2013.01);
(Continued)

(58) Field of Classification Search
None
See application file for complete search history.

(56) References Cited

U.S. PATENT DOCUMENTS

2009/0203977 A1 8/2009 Backman et al.
2011/0245642 A1* 10/2011 Minetoma ............ A61B 1/0638
600/324
(Continued)

FOREIGN PATENT DOCUMENTS

EP 2368487 9/2011
JP 2005157902 6/2005
(Continued)

OTHER PUBLICATIONS

"Office Action of Japan Counterpart Application," with machine English translation thereof, dated May 29, 2018, p. 1-p. 7.
(Continued)

*Primary Examiner* — Atiba O Fitzpatrick
(74) *Attorney, Agent, or Firm* — JCIPRNET

(57) ABSTRACT

An image processing apparatus includes: an image acquisition unit that acquires a plurality of endoscope images obtained by imaging an observation target at different times with an endoscope; a blood vessel extraction unit that extracts blood vessels of the observation target from the plurality of endoscope images; a blood vessel information calculation unit that calculates a plurality of pieces of blood vessel information for each of the blood vessels extracted from the endoscope images; a blood vessel parameter calculation unit that calculates a blood vessel parameter, which is relevant to the blood vessel extracted from each of the endoscope images, by calculation using the blood vessel information; and a blood vessel change index calculation unit that calculates a blood vessel change index, which indicates a temporal change of the blood vessel, using the blood vessel parameter.

11 Claims, 12 Drawing Sheets

(51) Int. Cl.
    *A61B 1/00* (2006.01)
    *A61B 1/04* (2006.01)
    *G02B 23/24* (2006.01)
    *G06T 7/90* (2017.01)
    *A61B 5/026* (2006.01)
    *A61B 5/1455* (2006.01)
    *A61B 1/005* (2006.01)
    *A61B 1/06* (2006.01)
    *A61B 8/06* (2006.01)

(52) U.S. Cl.
    CPC .......... *A61B 5/14552* (2013.01); *G02B 23/24* (2013.01); *G06T 7/90* (2017.01); *A61B 1/0052* (2013.01); *A61B 1/00188* (2013.01); *A61B 1/041* (2013.01); *A61B 1/0684* (2013.01); *A61B 8/06* (2013.01); *G06T 2207/10024* (2013.01); *G06T 2207/10068* (2013.01); *G06T 2207/30104* (2013.01)

(56) References Cited

U.S. PATENT DOCUMENTS

| | | | |
|---|---|---|---|
| 2012/0289801 A1 | 11/2012 | Yamaguchi | |
| 2015/0216425 A1* | 8/2015 | Gladshtein | A61B 3/1233 600/431 |
| 2016/0157763 A1 | 6/2016 | Tominaga | |
| 2016/0367154 A1* | 12/2016 | Gladshtein | F16L 33/30 |
| 2017/0296055 A1* | 10/2017 | Gardner | G01N 21/359 |

FOREIGN PATENT DOCUMENTS

| | | |
|---|---|---|
| JP | 2006218138 | 8/2006 |
| JP | 2007061638 | 3/2007 |
| JP | 2011142929 | 7/2011 |
| JP | 2011217798 | 11/2011 |
| JP | 2012514525 | 6/2012 |
| JP | 2012235926 | 12/2012 |
| JP | 2015066129 | 4/2015 |

OTHER PUBLICATIONS

"Search Report of Europe Counterpart Application", dated Oct. 9, 2018, p. 1-p. 6.

"International Search Report (Form PCT/ISA/210) of PCT/JP2016/078539," dated Dec. 20, 2016, with English translation thereof, pp. 1-5.

"International Preliminary Report on Patentability (Form PCT/IPEA/409) of PCT/JP2016/078539," completed on Sep. 28, 2017, with English translation thereof, pp. 1-7.

\* cited by examiner

IMAGE PROCESSING APPARATUS, ENDOSCOPE SYSTEM, AND IMAGE PROCESSING METHOD

CROSS-REFERENCE TO RELATED APPLICATIONS

This application is a Continuation of PCT International Application No. PCT/JP2016/078539 filed on 27 Sep. 2016, which claims priority under 35 U.S.C. § 119(a) to Japanese Patent Application No. 2015-189872 filed on 28 Sep. 2015. The above application is hereby expressly incorporated by reference, in its entirety, into the present application.

BACKGROUND OF THE INVENTION

1. Field of the Invention

The present invention relates to an image processing apparatus, an endoscope system, and an image processing method for calculating data, such as numerical values to be used for diagnosis, by using an endoscope image captured by an endoscope.

2. Description of the Related Art

In the medical field, diagnosis using an endoscope system including a light source device, an endoscope, and a processor device has been widely performed. In the diagnosis using the endoscope system, an insertion part of the endoscope is inserted into a subject, illumination light is emitted from the distal end portion, and an observation target irradiated with the illumination light (mucous membrane or the like inside the subject) is imaged by an imaging sensor mounted in the distal end portion of the endoscope. Then, an image (hereinafter, referred to as an endoscope image) of the observation target is generated using an image signal obtained by the imaging, and is displayed on the monitor.

Usually, in the endoscope system, an endoscope image in which the observation target can be observed with a natural color shade (hereinafter, referred to as a normal light image) is displayed by imaging the observation target irradiated with white illumination light (also referred to as normal light). In addition, an endoscope system that obtains an endoscope image (hereinafter, referred to as a special observation image) emphasizing a blood vessel, a pit pattern, and the like of the observation target by using light having a specific wavelength range as illumination light has also become widespread. In the case of performing diagnosis using an endoscope image, information of blood vessels, pit patterns, and the like is an important diagnostic material. Therefore, special observation images emphasizing these are particularly useful for diagnosis.

In recent years, an endoscope system or a diagnostic assistance apparatus is also known that assists a doctor's diagnosis by calculating the depth, thickness, density, and the like of blood vessels using an endoscope image (or an image signal used to generate an endoscope image) (JP2007-061638A and JP2011-217798A (corresponding to US2011/245642A1)). There is also known a system for displaying a temporal change in oxygen saturation on a monitor in real time (JP2012-235926A (corresponding to US2012/289801A1)) or a system for displaying a temporal change in fluorescence emitted from an observation target on a monitor (JP2015-066129A (corresponding to US2016/157763A1)).

SUMMARY OF THE INVENTION

As in JP2007-061638A and JP2011-217798A, information regarding blood vessels that can be calculated using an endoscope image (hereinafter, referred to as blood vessel information) is useful information for diagnosis. However, a doctor does not perform diagnosis based on only one of the pieces of blood vessel information, such as the depth, thickness, density, and the like of blood vessels, but performs diagnosis by considering a plurality of pieces of blood vessel information in a complex manner. For example, the thickness of the blood vessel and the density of the blood vessel are useful blood vessel information for diagnosis. However, the state of the observation target is not determined just because the thickness of the blood vessel is a specific thickness or the density of the blood vessel is a specific density, but diagnosis is performed by taking into consideration a plurality of pieces of blood vessel information, such as a case where the thickness of the blood vessel is equal to or greater than a specific thickness and the density of the blood vessel is equal to or greater than a specific value and accordingly the state of the observation target is a specific lesion.

In accordance with the actual condition of the multifaceted and complex diagnosis described above, in recent years, an endoscope system or an image processing apparatus for analyzing an endoscope image is required to assist a doctor's diagnosis by calculating more intuitive and useful information or the like than the blood vessel information calculated in the above JP2007-061638A and JP2011-217798A. Especially, how the state of the blood vessel of the observation target (distribution of thickness or depth) has temporally changed can become particularly useful information for diagnosis. Therefore, it is desirable that the endoscope system or the image processing apparatus calculates information that is more intuitive and useful than the blood vessel information and that indicates a temporal change in the state of the blood vessel.

In accordance with the actual condition of diagnosis using an endoscope image, it is an object of the present invention to provide an image processing apparatus, an endoscope system, and an image processing method for calculating a diagnostic assistance parameter (hereinafter, referred to as a blood vessel parameter) more useful than individual blood vessel information using a plurality of pieces of blood vessel information and calculating an index indicating a temporal change of a blood vessel of an observation target using the blood vessel parameter.

An image processing apparatus of the present invention comprises: an image acquisition unit that acquires a plurality of endoscope images obtained by imaging an observation target at different times with an endoscope; a blood vessel extraction unit that extracts blood vessels of the observation target from the plurality of endoscope images; a blood vessel information calculation unit that calculates a plurality of pieces of blood vessel information for each of the blood vessels extracted from the endoscope images; a blood vessel parameter calculation unit that calculates a blood vessel parameter, which is relevant to the blood vessel extracted from each of the endoscope images, by calculation using the blood vessel information; and a blood vessel change index calculation unit that calculates a blood vessel change index, which indicates a temporal change of the blood vessel of the observation target, using the blood vessel parameter.

It is preferable that the blood vessel information is the number of blood vessels, a thickness, a change in thickness, complexity of thickness change, a length, a change in length, the number of branches, a branching angle, a distance between branch points, the number of crossings, an inclination, an area, a density, a depth with respect to a mucous membrane as a reference, a height difference, an interval, a contrast, a color, a color change, a degree of meandering, blood concentration, oxygen saturation, a proportion of arteries, a proportion of veins, concentration of administered coloring agent, a running pattern, or a blood flow rate.

It is preferable that the blood vessel change index is a difference between the blood vessel parameters or a magnification or change rate of the blood vessel parameter.

It is preferable that the blood vessel information calculation unit calculates the blood vessel information for a region of interest set in a part or entirety of the endoscope image.

It is preferable that the blood vessel information is a statistic in the region of interest.

It is preferable that the blood vessel change index calculation unit calculates the blood vessel change index inductively in order of imaging times of the endoscope images.

It is preferable that the blood vessel change index calculation unit calculates the blood vessel change index by setting one of imaging times of the endoscope images as a reference time.

An endoscope system of the present invention comprises an endoscope that images an observation target and an image processing apparatus. The image processing apparatus has: an image acquisition unit that acquires a plurality of endoscope images obtained by imaging the observation target at different times with the endoscope; a blood vessel extraction unit that extracts blood vessels of the observation target from the plurality of endoscope images; a blood vessel information calculation unit that calculates a plurality of pieces of blood vessel information for each of the blood vessels extracted from the endoscope images; a blood vessel parameter calculation unit that calculates a blood vessel parameter, which is relevant to the blood vessel extracted from each of the endoscope images, by calculation using the blood vessel information; and a blood vessel change index calculation unit that calculates a blood vessel change index, which indicates a temporal change of the blood vessel of the observation target, using the blood vessel parameter.

An image processing method of the present invention comprises: a step in which an image acquisition unit acquires a plurality of endoscope images obtained by imaging an observation target at different times with an endoscope; a step in which a blood vessel extraction unit extracts blood vessels of the observation target from the plurality of endoscope images; a step in which a blood vessel information calculation unit calculates a plurality of pieces of blood vessel information for each of the blood vessels extracted from the endoscope images; a step in which a blood vessel parameter calculation unit calculates a blood vessel parameter, which is relevant to the blood vessel extracted from each of the endoscope images, by calculation using the blood vessel information; and a step in which a blood vessel change index calculation unit calculates a blood vessel change index, which indicates a temporal change of the blood vessel of the observation target, using the blood vessel parameter.

The image processing apparatus, the endoscope system, and the image processing method of the present invention calculate a blood vessel parameter, which serves as a guide for diagnosis more directly than individual blood vessel information, by calculation using a plurality of pieces of blood vessel information, and calculates a blood vessel change index, which indicates a temporal change of the blood vessel of the observation target, using the blood vessel parameter. Therefore, the image processing apparatus, the endoscope system, and the image processing method of the present invention can assist the doctor's diagnosis more directly than in the related art.

DESCRIPTION OF THE PREFERRED EMBODIMENTS

First Embodiment

Figure 1:
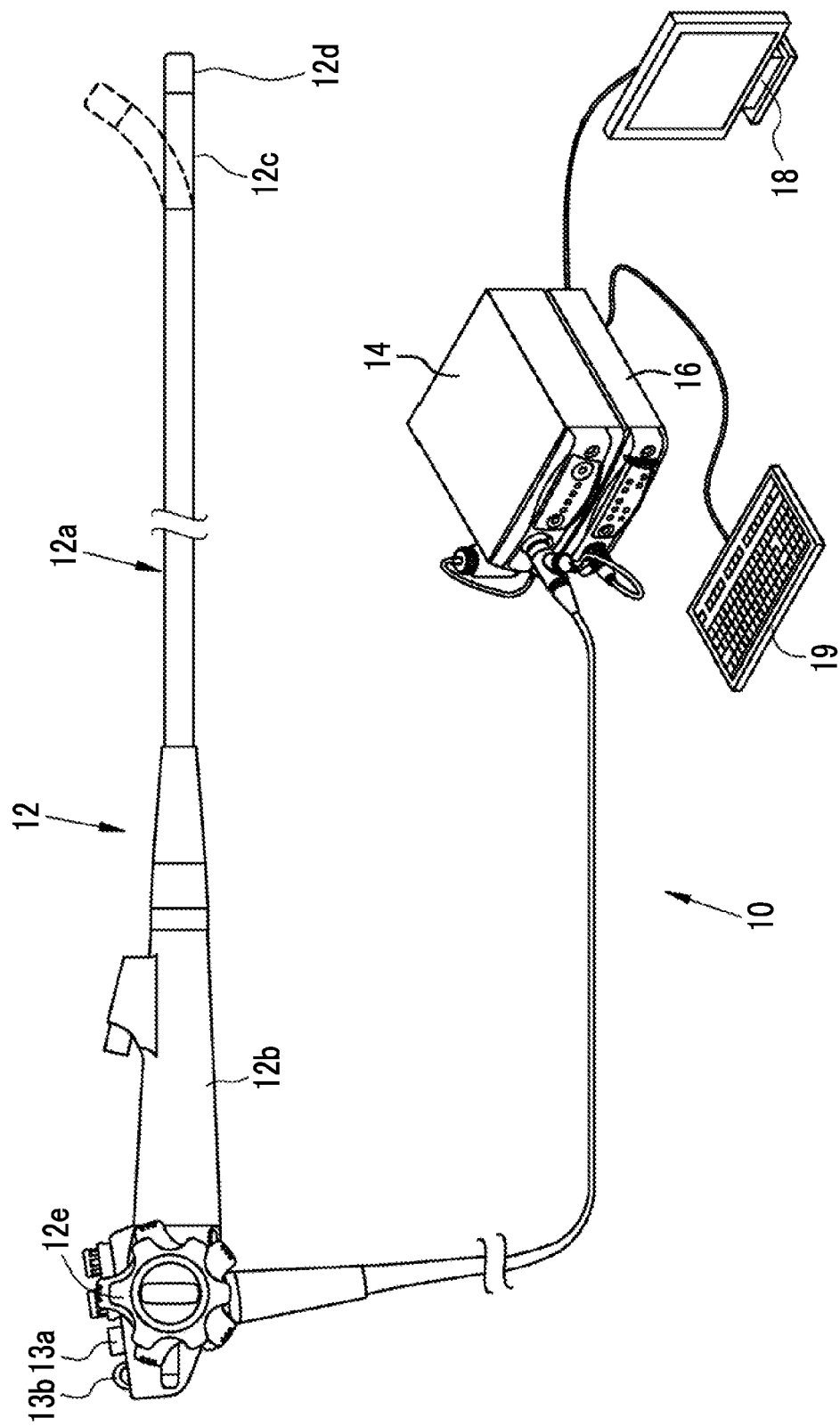
FIG. 1 is an external view of an endoscope system.

As shown in FIG. 1, an endoscope system 10 includes an endoscope 12, a light source device 14, a processor device 16, a monitor 18, and a console 19. The endoscope 12 is optically connected to the light source device 14, and is electrically connected to the processor device 16. The endoscope 12 includes an insertion part 12a that is inserted into a subject, an operation unit 12b provided in a proximal end portion of the insertion part 12a, and a bending portion 12c and a distal end portion 12d that are provided on the distal end side of the insertion part 12a. By operating an angle knob 12e of the operation unit 12b, the bending portion 12c is bent. Through the bending operation, the distal end portion 12d is directed in a desired direction.

In addition to the angle knob 12e, a still image acquisition instruction unit 13a and a zoom operation unit 13b are provided in the operation unit 12b. The still image acquisition instruction unit 13a operates in the case of inputting a still image acquisition instruction to the endoscope system 10. The instruction to acquire a still image includes a freeze instruction for displaying a still image of an observation target on the monitor 18 and a release instruction for storing a still image in a storage. The zoom operation unit 13b is used to input an imaging magnification change instruction for changing the imaging magnification.

The processor device 16 is electrically connected to the monitor 18 and the console 19. The monitor 18 output and displays an image of the observation target, information attached to the image, and the like. The console 19 functions as a user interface for receiving an input operation, such as a function setting.

Figure 2:
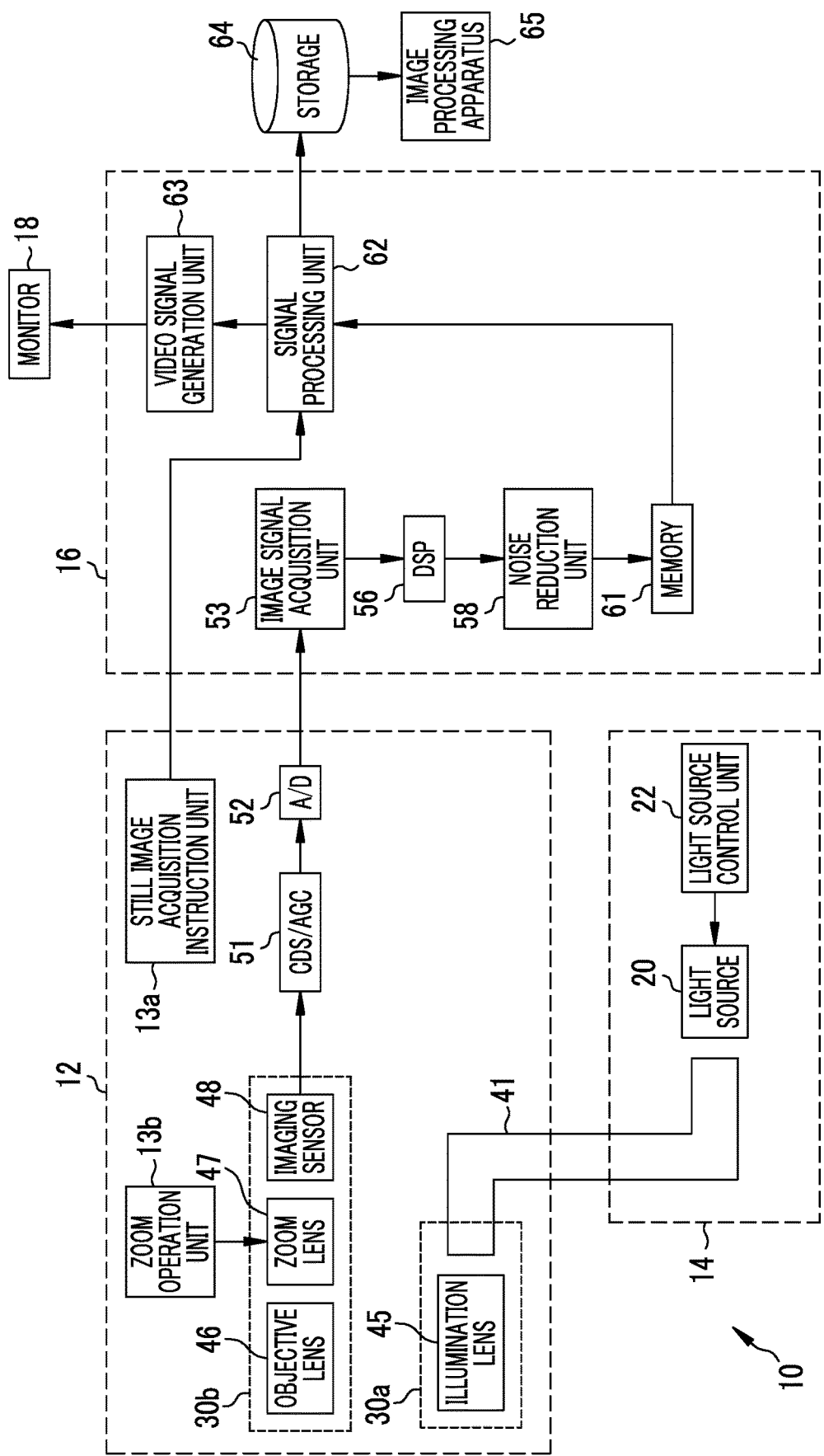
FIG. 2 is a block diagram of the endoscope system.

As shown in FIG. 2, the light source device 14 includes a light source 20 that emits illumination light to be emitted to the observation target and a light source control unit 22 that controls the light source 20. The light source 20 is, for example, a semiconductor light source such as a light emitting diode (LED) of a plurality of colors, a combination of a laser diode and a phosphor, or a halogen light source such as a xenon lamp. The light source 20 includes an optical filter for adjusting the wavelength range of light emitted from the LED or the like. The light source control unit 22 controls the amount of illumination light by ON/OFF of the LED or the like or by adjusting the driving current or the driving voltage of the LED or the like. In addition, the light source control unit 22 controls the wavelength range of illumination light by changing the optical filter or the like.

The endoscope system 10 has two types of observation modes, that is, a normal observation mode for observing an observation target in a normal observation image and a special observation mode for observing an observation target in a special observation image. In a case where the observation mode is a normal observation mode, the light source control unit 22 causes the light source 20 to generate approximately white illumination light. In a case where the observation mode is a special observation mode, the light source control unit 22 causes the light source 20 to generate illumination light having a specific narrow wavelength range (hereinafter, referred to as narrowband light). The observation mode is switched by a mode change switch (not shown) provided in the operation unit 12b.

The illumination light emitted from the light source 20 is incident on a light guide 41 inserted into the insertion part 12a. The light guide 41 is built into the endoscope 12 and a universal cord, and propagates the illumination light to the distal end portion 12d of the endoscope 12. The universal cord is a cord for connecting the endoscope 12 with the light source device 14 and the processor device 16. As the light guide 41, it is possible to use a multi-mode fiber. As an example, it is possible to use a small-diameter fiber cable having a diameter of ϕ0.3 mm to ϕ0.5 mm that includes a core with a diameter of 105 µm, a cladding with a diameter of 125 µm, and a protective layer as an outer skin.

An illumination optical system 30a and an imaging optical system 30b are provided in the distal end portion 12d of the endoscope 12. The illumination optical system 30a has an illumination lens 45, and the illumination light propagated by the light guide 41 is emitted to the observation target through the illumination lens 45. The imaging optical system 30b has an objective lens 46, a zoom lens 47, and an imaging sensor 48. Various kinds of light, such as reflected light, scattered light, and fluorescence from the observation target, are incident on the imaging sensor 48 through the objective lens 46 and the zoom lens 47. As a result, an image of the observation target is formed on the imaging sensor 48. The zoom lens 47 is moved freely between the telephoto end and the wide end by operating the zoom operation unit 13b, thereby enlarging or reducing the observation target formed on the imaging sensor 48.

The imaging sensor 48 is a color imaging sensor in which any one of red (R), green (G), and blue (B) color filters is provided for each pixel, and images the observation target and outputs the image signals of the respective colors of RGB. As the imaging sensor 48, it is possible to use a charge coupled device (CCD) imaging sensor or a complementary metal oxide semiconductor (CMOS) imaging sensor. Instead of the imaging sensor 48 in which primary color filters are provided, a complementary color imaging sensor including complementary color filters of cyan (C), magenta (M), yellow (Y), and green (G) may be used. In a case where a complementary color imaging sensor is used, image signals of four colors of CMYG are output. Therefore, by converting the image signals of four colors of CMYG into image signals of three colors of RGB by complementary color-primary color conversion, it is possible to obtain the same RGB image signals as in the imaging sensor 48. Instead of the imaging sensor 48, a monochrome sensor in which no color filter is provided may be used.

The image signal output from the imaging sensor 48 is transmitted to a CDS/AGC circuit 51. The CDS/AGC circuit 51 performs correlated double sampling (CDS) or automatic gain control (AGC) for the image signal that is an analog signal. The image signal transmitted through the CDS/AGC circuit 51 is converted into a digital image signal by an analog to digital (A/D) converter 52. The digital image signal after A/D conversion is input to the processor device 16.

The processor device 16 includes an image signal acquisition unit 53, a digital signal processor (DSP) 56, a noise reduction unit 58, a memory 61, a signal processing unit 62, and a video signal generation unit 63.

The image signal acquisition unit 53 acquires a digital image signal from the endoscope 12. The DSP 56 performs various kinds of signal processing, such as defect correction processing, offset processing, gain correction processing, linear matrix processing, gamma conversion processing, and demosaic processing, on the image signal acquired by the image signal acquisition unit 53. In the defect correction processing, the signal of a defective pixel of the imaging sensor 48 is corrected. In the offset processing, a dark current component is removed from the image signal subjected to the defect correction processing, and an accurate zero level is set. In the gain correction processing, the signal level is adjusted by multiplying the image signal after the offset processing by a specific gain.

Linear matrix processing for increasing color reproducibility is performed on the image signal after the gain correction processing. Then, the brightness or saturation is adjusted by gamma conversion processing. Demosaic processing (also referred to as isotropic processing or synchronization processing) is performed on the image signal after the gamma conversion processing, and the signal of missing color in each pixel is generated by interpolation. Through the demosaic processing, all pixels have signals of RGB colors. The noise reduction unit 58 reduces noise by performing noise reduction processing on the image signal subjected to the demosaic processing or the like by the DSP 56 using, for example, a moving average method or a median filter method. The image signal from which noise has been reduced is stored in the memory 61.

The signal processing unit 62 acquires the image signal after noise reduction from the memory 61. Then, image processing, such as color conversion processing, color emphasis processing, and structure emphasis processing, is performed on the acquired image signal as necessary, thereby generating a color endoscope image in which the observation target is reflected. The color conversion processing is a process of performing color conversion on the image signal by 3×3 matrix processing, gradation conversion processing, three-dimensional look-up table (LUT)

processing, and the like. The color emphasis processing is performed on the image signal after the color conversion processing. The structure emphasis processing is a process of emphasizing a specific tissue or structure included in an observation target, such as a blood vessel or a pit pattern, and is performed on the image signal after the color emphasis processing. Since the endoscope image generated by the signal processing unit 62 is a normal observation image in a case where the observation mode is a normal observation mode and is a special observation image in a case where the observation mode is a special observation mode, the content of the color conversion processing, the color emphasis processing, and the structure emphasis processing differs depending on the observation mode. In the case of the normal observation mode, the signal processing unit 62 generates a normal observation image by performing the above-described various kinds of signal processing by which the observation target has a natural color shade. In the case of the special observation mode, the signal processing unit 62 generates a special observation image by performing the above-described various kinds of signal processing for emphasizing at least a blood vessel of the observation target. In the special observation image generated by the signal processing unit 62, a blood vessel (so-called surface layer blood vessel) located at a relatively shallow position inside the observation target with the surface of the mucous membrane as a reference has a magenta type color (for example, brown color), and a blood vessel located at a relatively deep position inside the observation target with the surface of the mucous membrane as a reference (so-called middle deep layer blood vessel) has a cyan type color (for example, green color). For this reason, the blood vessel of the observation target is emphasized due to the color difference with respect to the mucous membrane expressed by a pink type color.

The signal processing unit 62 inputs the generated endoscope image to the video signal generation unit 63. The video signal generation unit 63 converts the endoscope image into a video signal to be output and displayed on the monitor 18. In a case where a release instruction is input by operating the still image acquisition instruction unit 13*a*, the signal processing unit 62 stores the generated endoscope image in a storage 64. The storage 64 is an external storage device connected to the processor device 16 through a local area network (LAN). For example, the storage 64 is a file server of a system for filing an endoscope image, such as a picture archiving and communication system (PACS), or a network attached storage (NAS). The endoscope image stored in the storage 64 is used by an image processing apparatus 65.

Figure 3:
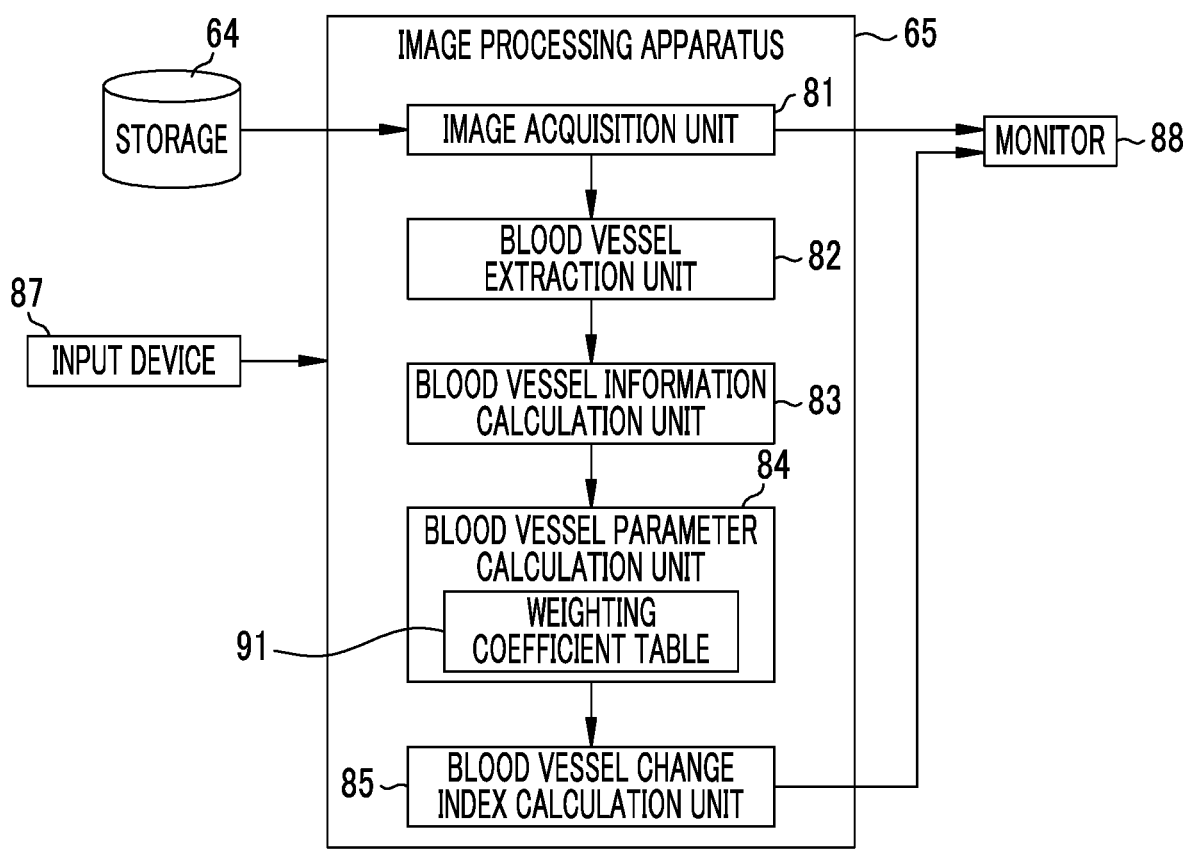
FIG. 3 is a block diagram of an image processing apparatus.

The image processing apparatus 65 is an apparatus that performs image processing on the endoscope image to calculate a blood vessel parameter for diagnostic assistance and calculate a blood vessel change index using the blood vessel parameter. As shown in FIG. 3, the image processing apparatus 65 includes an image acquisition unit 81, a blood vessel extraction unit 82, a blood vessel information calculation unit 83, a blood vessel parameter calculation unit 84, and a blood vessel change index calculation unit 85. An input device 87 including a keyboard and a pointing device used for designating a region of interest (ROI) or a monitor 88 for displaying an endoscope image and the like is connected to the image processing apparatus 65.

The image acquisition unit 81 acquires a plurality of endoscope images, which are obtained by imaging the observation target at different times by the endoscope 12, from the storage 64. Endoscope images stored in the storage 64 include a normal observation image and a special observation image. In the present embodiment, the image acquisition unit 81 acquires a special observation image emphasizing the blood vessel from the storage 64.

Figure 4:
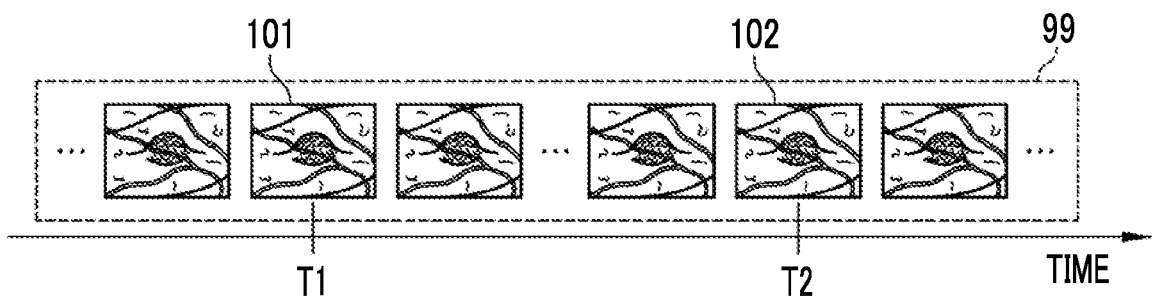
FIG. 4 is an explanatory diagram showing an endoscope image stored in a storage.

As shown in FIG. 4, a plurality of endoscope images 99 obtained by imaging the observation target at different times (different dates and times) are stored in the storage 64. The image acquisition unit 81 acquires a plurality of endoscope images, which are obtained by imaging at different times, from the plurality of endoscope images 99 according to a setting input or the like by the user. In the present embodiment, for the sake of simplicity, a first endoscope image 101 and a second endoscope image 102 are acquired. The first endoscope image 101 is an endoscope image obtained by imaging the observation target earlier than the second endoscope image 102. Conversely, the second endoscope image 102 is an endoscope image obtained by imaging the observation target later than the first endoscope image 101. That is, "first" and "second" indicate the order of the endoscope image acquisition time. Between two endoscope images acquired by the image acquisition unit 81, an endoscope image obtained by imaging the observation target relatively earlier is the first endoscope image 101, and an endoscope image obtained by imaging the observation target relatively later is the second endoscope image 102. In a case where the imaging time T1 of the first endoscope image 101 is compared with the imaging time T2 of the second endoscope image 102, T1<T2 is satisfied.

The blood vessel extraction unit 82 extracts blood vessels of the observation target from each of the plurality of endoscope images acquired by the image acquisition unit 81. The blood vessel extraction method is, for example, frequency filtering. In the present embodiment, since the image acquisition unit 81 acquires the two endoscope images of the first endoscope image 101 and the second endoscope image 102, the blood vessel extraction unit 82 extracts blood vessels of the observation target from each of the first endoscope image 101 and the second endoscope image 102. Hereinafter, the blood vessel extracted from the first endoscope image 101 is referred to as a first blood vessel, and the blood vessel extracted from the second endoscope image 102 is referred to as a second blood vessel. In the present embodiment, the blood vessel extraction unit 82 extracts blood vessels from the entire endoscope image acquired by the image acquisition unit 81. However, in a case where a region of interest is designated, blood vessels may be extracted only within the designated region of interest.

The blood vessel information calculation unit 83 calculates a plurality of pieces of blood vessel information for each of the blood vessels extracted from the endoscope image. The blood vessel information is, for example, the number of blood vessels, the number of branches, a branching angle, a distance between branch points, the number of crossings, a thickness, a change in thickness, complexity of thickness change, a length, an interval, a depth with respect to a mucous membrane as a reference, a height difference, an inclination, an area, a density, a contrast, a color, color change, degree of meandering, blood concentration, oxygen saturation, proportion of arteries, proportion of veins, concentration of administered coloring agent, a running pattern, or a blood flow rate. In the present embodiment, the blood vessel information calculation unit 83 calculates all the pieces of the above-described blood vessel information as far as possible. However, it is possible to calculate the blood vessel information by selecting the required blood vessel information from the above. The above-described blood vessel information is an example, and information regarding other blood vessels may be calculated as blood vessel information.

The number of blood vessels is the number of blood vessels extracted in the entire endoscope image or in a region of interest. The number of blood vessels is calculated using, for example, the number of branch points (the number of branches) of the extracted blood vessel, the number of intersections (the number of crossings) with other blood vessels, and the like. The branching angle of a blood vessel is an angle formed by two blood vessels at a branching point. The distance between branch points is a linear distance between an arbitrary branch point and a branch point adjacent thereto or a length along a blood vessel from an arbitrary branch point to a branch point adjacent thereto.

The number of crossings between blood vessels is the number of intersections at which blood vessels having different submucosal depths cross each other on the endoscope image. More specifically, the number of crossings between blood vessels is the number of blood vessels, which are located at relatively shallow submucosal positions, crossing blood vessels located at deep positions.

The thickness of a blood vessel (blood vessel diameter) is a distance between the blood vessel and the boundary of the mucous membrane. For example, the thickness of a blood vessel (blood vessel diameter) is measured by counting the number of pixels along the lateral direction of the blood vessel from the edge of the extracted blood vessel through the blood vessel. Therefore, the thickness of a blood vessel is the number of pixels. However, in a case where the imaging distance, zoom magnification and the like at the time of capturing an endoscope image are known, the number of pixels can be converted into a unit of length, such as "μm", as necessary.

The change in the thickness of a blood vessel is blood vessel information regarding a variation in the thickness of the blood vessel, and is also referred to as the aperture inconsistency. The change in the thickness of a blood vessel is, for example, a change rate of the blood vessel diameter (also referred to as the degree of expansion). Using the thickness (minimum diameter) of the thinnest portion of the blood vessel and the thickness (maximum diameter) of the thickest portion of the blood vessel, the change rate of the blood vessel diameter is calculated as "blood vessel diameter change rate (%)=minimum diameter/maximum diameter×100".

In a case where an endoscope image obtained by imaging the observation target in a past examination and an endoscope image obtained by imaging the same observation target in a subsequent new examination are used, a temporal change in the thickness of the same blood vessel extracted from the endoscope image obtained by the subsequent new examination with respect to the thickness of the blood vessel extracted from the endoscope image obtained by the past examination may be the change in the thickness of the blood vessel.

As a change in the thickness of the blood vessel, a proportion of a small diameter portion or a proportion of a large diameter portion may be calculated. The small diameter portion is a portion whose thickness is equal to or less than the threshold value, and the large diameter portion is a portion where the thickness is equal to or greater than the threshold value. The proportion of a small diameter portion is calculated as "proportion of small diameter portion (%)=length of small diameter portion/length of blood vessel×100". Similarly, the proportion of a large diameter portion is calculated as "proportion of large diameter portion (%)=length of large diameter portion/length of blood vessel×100".

The complexity of the change in the thickness of a blood vessel (hereinafter, referred to as the "complexity of the thickness change") is blood vessel information indicating how complex the change is in a case where the thickness of the blood vessel changes, and is blood vessel information calculated by combining a plurality of pieces of blood vessel information indicating the change in the thickness of the blood vessel (that is, the change rate of the blood vessel diameter, the proportion of the small diameter portion, or the proportion of the large diameter portion). The complexity of the thickness change can be calculated, for example, by the product of the change rate of the blood vessel diameter and the proportion of the small diameter portion.

The length of a blood vessel is the number of pixels counted along the longitudinal direction of the extracted blood vessel.

The interval between blood vessels is the number of pixels showing the mucous membrane between the edges of the extracted blood vessels. In the case of one extracted blood vessel, the interval between blood vessels has no value.

The depth of a blood vessel is measured with the mucous membrane (more specifically, the surface of the mucous membrane) as a reference. The depth of a blood vessel with the mucous membrane as a reference can be calculated based on, for example, the color of the blood vessel. In the case of the special observation image, a blood vessel located near the surface of the mucous membrane is expressed by a magenta type color, and a blood vessel far from the surface of the mucous membrane and located at a deep submucosal position is expressed by a cyan type color. Therefore, the blood vessel information calculation unit 83 calculates the depth of the blood vessel with the mucous membrane as a reference for each pixel based on the balance of the signals of the respective colors of R, G, and B of the pixels extracted as a blood vessel.

The height difference of a blood vessel is the magnitude of the difference in the depth of the blood vessel. For example, the height difference of one blood vessel of interest is calculated by the difference between the depth (maximum depth) of the deepest portion of the blood vessel and the depth (minimum depth) of the shallowest portion. In a case where the depth is constant, the height difference is zero.

The inclination of a blood vessel is the change rate of the depth of the blood vessel, and is calculated using the length of the blood vessel and the depth of the blood vessel. That is, the inclination of a blood vessel is calculated as "inclination of blood vessel=depth of blood vessel/length of blood vessel". The blood vessel may be divided into a plurality of sections, and the inclination of the blood vessel may be calculated in each section.

The area of a blood vessel is the number of pixels extracted as a blood vessel or a value proportional to the number of pixels extracted as a blood vessel. The area of a blood vessel is calculated within the region of interest, outside the region of interest, or for the entire endoscope image.

The density of blood vessels is a proportion of blood vessels in a unit area. A region of a specific size (for example, a region of a unit area) including pixels for calculating the density of blood vessels at its approximate center is cut out, and the proportion of blood vessels occupying all the pixels within the region is calculated. By performing this on all the pixels of the region of interest or the entire endoscope image, the density of blood vessels of each pixel can be calculated.

The contrast of a blood vessel is a relative contrast with respect to the mucous membrane of the observation target. The contrast of a blood vessel is calculated as, for example, "$Y_V/Y_M$" or "$(Y_V-Y_M)/(Y_V+Y_M)$", using the brightness $Y_V$ of the blood vessel and the brightness $Y_M$ of the mucous membrane.

The color of a blood vessel is each value of RGB of pixels showing the blood vessel. The change in the color of a blood vessel is a difference or ratio between the maximum value and the minimum value of the RGB values of pixels showing the blood vessel. For example, the ratio between the maximum value and the minimum value of the B value of a pixel showing the blood vessel, the ratio between the maximum value and the minimum value of the G value of a pixel showing the blood vessel, or the ratio between the maximum value and the minimum value of the R value of a pixel showing the blood vessel indicates a change in the color of the blood vessel. Needless to say, conversion into complementary colors may be performed to calculate the color of the blood vessel and a change in the color of the blood vessel for each value of cyan, magenta, yellow, green, and the like.

The degree of meandering of a blood vessel is blood vessel information indicating the size of a range in which the blood vessel travels while meandering. The degree of meandering of a blood vessel is, for example, the area (the number of pixels) of a minimum rectangle including the blood vessel for which the degree of meandering is to be calculated. The ratio of the length of the blood vessel to the linear distance between the start point and the end point of the blood vessel may be used as the degree of meandering of the blood vessel.

The blood concentration of a blood vessel is blood vessel information proportional to the amount of hemoglobin contained in a blood vessel. Since the ratio (G/R) of the G value to the R value of a pixel showing a blood vessel is proportional to the amount of hemoglobin, the blood concentration can be calculated for each pixel by calculating the value of G/R.

The oxygen saturation of a blood vessel is the amount of oxygenated hemoglobin to the total amount of hemoglobin (total amount of oxygenated hemoglobin and reduced hemoglobin). The oxygen saturation can be calculated by using an endoscope image obtained by imaging the observation target with light in a specific wavelength range (for example, blue light having a wavelength of about 470±10 nm) having a large difference between the light absorption coefficients of oxygenated hemoglobin and reduced hemoglobin. In a case where blue light having a wavelength of about 470±10 nm is used, the B value of the pixel showing the blood vessel is correlated with the oxygen saturation. Therefore, by using a table or the like that associates the B value with the oxygen saturation, it is possible to calculate the oxygen saturation of each pixel showing the blood vessel.

The proportion of arteries is the ratio of the number of pixels of arteries to the number of pixels of all the blood vessels. Similarly, the proportion of veins is the ratio of the number of pixels of veins to the number of pixels of all the blood vessels. Arteries and veins can be distinguished by oxygen saturation. For example, assuming that a blood vessel having an oxygen saturation of 70% or more is an artery and a blood vessel having an oxygen saturation less than 70% is a vein, extracted blood vessels can be divided into arteries and veins. Therefore, the proportion of arteries and the proportion of veins can be calculated.

The concentration of an administered coloring agent is the concentration of a coloring agent sprayed on the observation target or the concentration of a coloring agent injected into the blood vessel by intravenous injection. The concentration of the administered coloring agent is calculated, for example, by the ratio of the pixel value of the coloring agent color to the pixel value of a pixel other than the coloring agent color. For example, in a case where a coloring agent for coloring in blue is administered, B/G, B/R, and the like indicate the concentration of the coloring agent fixed (or temporarily adhered) to the observation target.

The traveling pattern of a blood vessel is blood vessel information regarding the traveling direction of a blood vessel. The traveling pattern of a blood vessel is, for example, an average angle (traveling direction) of a blood vessel with respect to a reference line arbitrarily set, a dispersion (variation in traveling direction) of an angle formed by a blood vessel with respect to a reference line set arbitrarily, and the like.

The blood flow rate (also referred to as a blood flow speed) of a blood vessel is the number of red blood cells that can pass per unit time. In a case where an ultrasound probe is used together through the forceps channel of the endoscope 12 or the like, the Doppler shift frequency of each pixel showing the blood vessel of the endoscope image can be calculated by using the signal obtained by the ultrasound probe. The blood flow rate of the blood vessel can be calculated by using the Doppler shift frequency.

By operating the input device 87, it is possible to set a region of interest in the entirety or a part of the endoscope image. For example, in a case where a part of the endoscope image is set as a region of interest, the blood vessel information calculation unit 83 calculates blood vessel information within the region of interest. In a case where a region of interest is not designated or a case where the entire endoscope image is set as a region of interest, the blood vessel information calculation unit 83 calculates blood vessel information by setting the entire endoscope image as a region of interest.

The blood vessel information calculation unit 83 calculates blood vessel information for each pixel of the endoscope image. For example, blood vessel information of one pixel is calculated using the data of pixels in a predetermined range including a pixel whose blood vessel information is to be calculated (for example, a range of 99×99 pixels centered on the pixel whose blood vessel information is to be calculated). For example, in the case of calculating the thickness of a blood vessel as blood vessel information, the "thickness of a blood vessel" for each pixel is a statistic of the thickness of a blood vessel in the predetermined range. The statistic is a so-called basic statistic, and is, for example, a maximum value, a minimum value, an average value, a median, or a mode. Needless to say, it is also possible to use statistics other than the exemplified values. For example, a value (ratio between the maximum value and the minimum value or the like) calculated using a so-called representative value, such as the maximum value, the minimum value, the average value, the median, or the mode, or a so-called scattering degree, such as a dispersion, a standard deviation, and a variation coefficient, can be used.

In the case of setting a region of interest, the blood vessel information calculation unit 83 calculates a statistic of blood vessel information of each pixel included in the region of interest, and sets the value as blood vessel information of the region of interest. For example, in the case of calculating the thickness of a blood vessel as blood vessel information, the "thickness of a blood vessel" of each pixel is calculated as described above. In a case where a region of interest is set, a statistic of the "thickness of a blood vessel" of each pixel included in the region of interest is further calculated, and one "thickness of a blood vessel" is calculated for one set region of interest. The same is true for a case where the entire endoscope image is set as a region of interest.

The statistic in the case of calculating blood vessel information for each pixel and the statistic in the case of calculating blood vessel information of a region of interest may be the same statistic, or may be different. For example, in the case of calculating the thickness of a blood vessel for each pixel, an average value of the thickness of the blood vessel appearing in a "predetermined range" may be calculated. Thereafter, even in the case of calculating the thickness of a blood vessel in the region of interest, the average value of the thickness of the blood vessel of each pixel may be calculated, or a mode of the thickness of the blood vessel of each pixel may be calculated.

In the present embodiment, blood vessel information is calculated for each pixel as described above and then the statistic of the blood vessel information calculated for each pixel within the region of interest is calculated, thereby calculating the blood vessel information of the region of interest. However, depending on the type of blood vessel information to be calculated, a relationship between the method of calculating the statistic in the case of calculating the blood vessel information for each pixel and the method of calculating the statistic in the case of calculating the blood vessel information of the region of interest, and the like, it is possible to omit the blood vessel information for each pixel. In the case of the "thickness of a blood vessel", an average value of the thickness of the blood vessel appearing in the region of interest can be set as the thickness of the blood vessel in the region of interest.

In the present embodiment, the blood vessel extraction unit 82 extracts blood vessels from each of the first endoscope image 101 and the second endoscope image 102. Therefore, the blood vessel information calculation unit 83 calculates a plurality of pieces of blood vessel information for the first blood vessel extracted from the first endoscope image 101. Hereinafter, the blood vessel information calculated for the first blood vessel is referred to as first blood vessel information. That is, the blood vessel information calculation unit 83 calculates a plurality of pieces of first blood vessel information for the first blood vessel. In a case where a region of interest is set in a part or the entirety of the first endoscope image 101, each piece of the first blood vessel information is a statistic in the set region of interest.

Similarly, the blood vessel information calculation unit 83 calculates a plurality of pieces of blood vessel information for the second blood vessel extracted from the second endoscope image 102. Hereinafter, the blood vessel information calculated for the second blood vessel is referred to as second blood vessel information. That is, the blood vessel information calculation unit 83 calculates a plurality of pieces of second blood vessel information for the second blood vessel. In a case where a region of interest is set in a part or the entirety of the second endoscope image 102, each piece of the second blood vessel information is a statistic in the set region of interest.

The "plurality of pieces of first blood vessel information" and the "plurality of pieces of second blood vessel information" calculated as described above by the blood vessel information calculation unit 83 are the same in kind (combination of kinds). For example, in a case where the blood vessel information calculation unit 83 calculates three kinds of blood vessel information of "thickness", "depth", and "density" as the first blood vessel information for the first blood vessel, the blood vessel information calculation unit 83 also calculates three kinds of blood vessel information of "thickness", "depth", and "density" as the second blood vessel information for the second blood vessel.

The blood vessel parameter calculation unit 84 calculates a blood vessel parameter, which is relevant to the blood vessel extracted from each endoscope image, by calculation using the blood vessel information. The blood vessel parameter is obtained by calculation using a plurality of pieces of blood vessel information, and is an evaluation value for evaluating the observation target (or blood vessels of the observation target). In the present embodiment, the blood vessel parameter calculation unit 84 calculates a first blood vessel parameter P1 relevant to the first blood vessel, by calculation using a plurality of pieces of first blood vessel information. The blood vessel parameter calculation unit 84 calculates a second blood vessel parameter P2 relevant to the second blood vessel by calculation using a plurality of pieces of second blood vessel information.

The blood vessel parameter calculation unit 84 calculates the first blood vessel parameter P1 by multiplying each of the plurality of pieces of first blood vessel information by a weighting coefficient and taking a sum thereof. The weighting coefficient is stored in a weighting coefficient table 91, and is determined in advance, for example, by machine learning. The calculation for calculating the second blood vessel parameter P2 using a plurality of pieces of second blood vessel information is the same as the calculation for calculating the first blood vessel parameter P1, and the weighting coefficient to be used is also the weighting coefficient table 91 used for the calculation of the first blood vessel parameter P1.

The first blood vessel parameter P1 and the second blood vessel parameter P2 are the same kind of evaluation values for evaluating the state of the blood vessel of the observation target using the same method (by the same calculation). That is, both the first blood vessel parameter P1 and the second blood vessel parameter P2 are the same blood vessel parameters, and "first" and "second" merely indicate that a blood vessel, for which the blood vessel parameters have been calculated, is the first blood vessel extracted from the first endoscope image 101 or the second blood vessel extracted from the second endoscope image 102. Needless to say, the values of the first blood vessel parameter P1 and the second blood vessel parameter P2 are basically different values unless the values of the first blood vessel parameter P1 and the second blood vessel parameter P2 match each other by chance. The difference between the values of the first blood vessel parameter P1 and the second blood vessel parameter P2 is a difference between the imaging time T1 of the first endoscope image 101 and the imaging time T2 of the second endoscope image 102.

In the present embodiment, the blood vessel parameter calculation unit 84 calculates the weighted sum of a plurality of pieces of blood vessel information as a blood vessel parameter as described above, the method of calculating the blood vessel parameter is arbitrary. For example, a blood vessel parameter may be calculated by operation including addition, subtraction, multiplication, and division instead of simply taking a sum, or a blood vessel parameter may be calculated using other functions.

Since the blood vessel parameters are calculated by adding pieces of blood vessel information having different dimensions (units) or the like, the blood vessel parameters have no physical meaning but function as indices of diagnosis. That is, unlike the blood vessel information, the blood vessel parameter is a value having no physical meaning.

The blood vessel change index calculation unit 85 calculates a blood vessel change index 108 (refer to FIG. 5) using the blood vessel parameters calculated by the blood vessel parameter calculation unit 84. In the present embodiment, since the blood vessel parameter calculation unit 84 calculates the first blood vessel parameter P1 and the second blood vessel parameter P2, the blood vessel change index calculation unit 85 calculates the blood vessel change index 108 using the first blood vessel parameter P1 and the second blood vessel parameter P2.

The blood vessel change index 108 is an index indicating a temporal change of a blood vessel of the observation target. For example, the blood vessel change index 108 is a difference between blood vessel parameters or the magnification or change rate of each blood vessel parameter. The "temporal change of a blood vessel" includes a change due to passage of time (change over time), a change due to spraying, application, injection, administration, and the like of a medicine, and other changes after treatment. Taking the elapsed time into consideration, the difference, magnification, or change rate per unit time may be used as the blood vessel change index 108. The unit time is 1 year, 1 month, 1 day, 1 hour, 1 minute, 1 second, or the like.

In the case of the present embodiment, since the difference between the values of the first blood vessel parameter P1 and the second blood vessel parameter P2 is the difference between the imaging time T1 of the first endoscope image 101 and the imaging time T2 of the second endoscope image 102, the change in the second blood vessel parameter with respect to the first blood vessel parameter indicates a temporal change of the blood vessel of the observation target. Therefore, the blood vessel change index calculation unit 85 calculates the change in the second blood vessel parameter P2 with respect to the first blood vessel parameter P1 as the blood vessel change index 108.

In the present embodiment, the blood vessel change index calculation unit 85 calculates any of a difference $\Delta$ between the first blood vessel parameter P1 and the second blood vessel parameter P2, a magnification Rm of the second blood vessel parameter P2 with respect to the first blood vessel parameter P1, or a change rate Rc of the second blood vessel parameter P2 with respect to the first blood vessel parameter P1. The difference $\Delta$ between the first blood vessel parameter P1 and the second blood vessel parameter P2 is $\Delta$=P2−P1. The magnification Rm of the second blood vessel parameter P2 with respect to the first blood vessel parameter P1 is Rm=P2/P1. The change rate Rc of the second blood vessel parameter P2 with respect to the first blood vessel parameter P1 is Rc=(P2−P1)/P1. The difference $\Delta$, the magnification Rm, and the change rate Rc are examples, and the blood vessel change index calculation unit 85 may calculate the blood vessel change index 108 using a method other than the difference $\Delta$, the magnification Rm, or the change rate Rc. For example, a difference per unit time $\Delta$/dT can be set as the blood vessel change index 108 by dividing the difference $\Delta$ by a time difference dT (=T2−T1) between the imaging time T1 of the first endoscope image 101 and the imaging time T2 of the second endoscope image 102. Similarly, the magnification Rm or the change rate Rc per unit time can be calculated.

Figure 5:
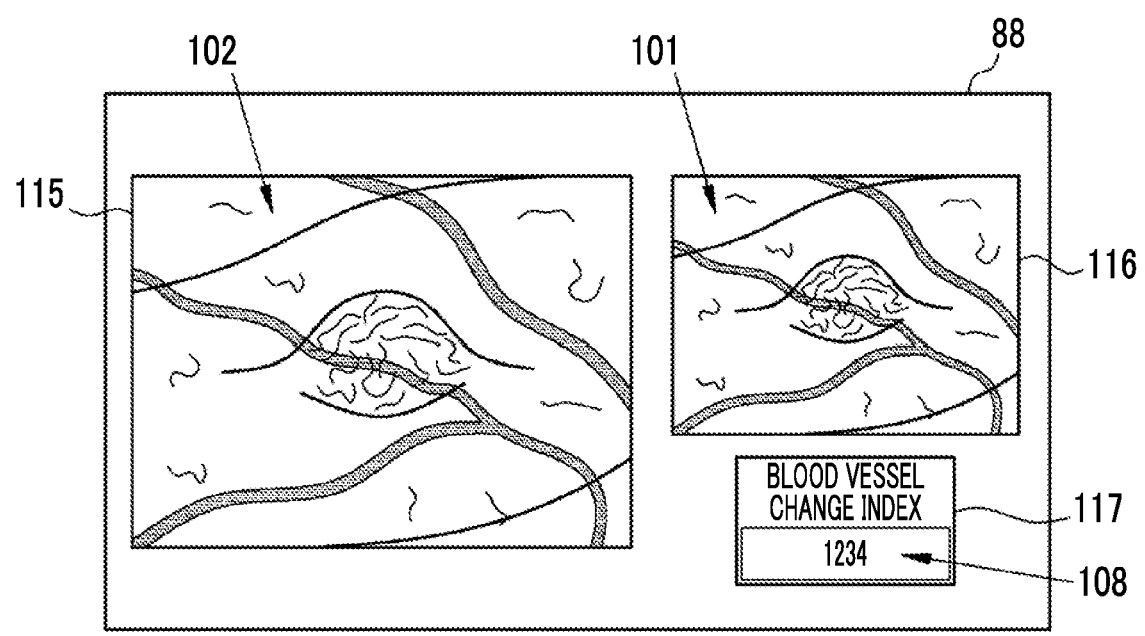
FIG. 5 is a display screen of a monitor.

The image processing apparatus 65 displays the first endoscope image 101 and the second endoscope image 102 acquired by the image acquisition unit 81 and the blood vessel change index 108 calculated by the blood vessel change index calculation unit 85 on the monitor 88. As shown in FIG. 5, the monitor 88 has a main window 115, a subwindow 116, and a blood vessel change index display portion 117. The main window 115 and the subwindow 116 display endoscope images, and the blood vessel change index display portion 117 displays the blood vessel change index 108. The main window 115 is a region for displaying an endoscope image obtained by imaging the observation target relatively later, and the subwindow 116 is a region for displaying an endoscope image obtained by imaging the observation target relatively earlier. Therefore, the image processing apparatus 65 displays the second endoscope image 102 on the main window 115, and displays the first endoscope image 101 on the subwindow 116.

Figure 6:
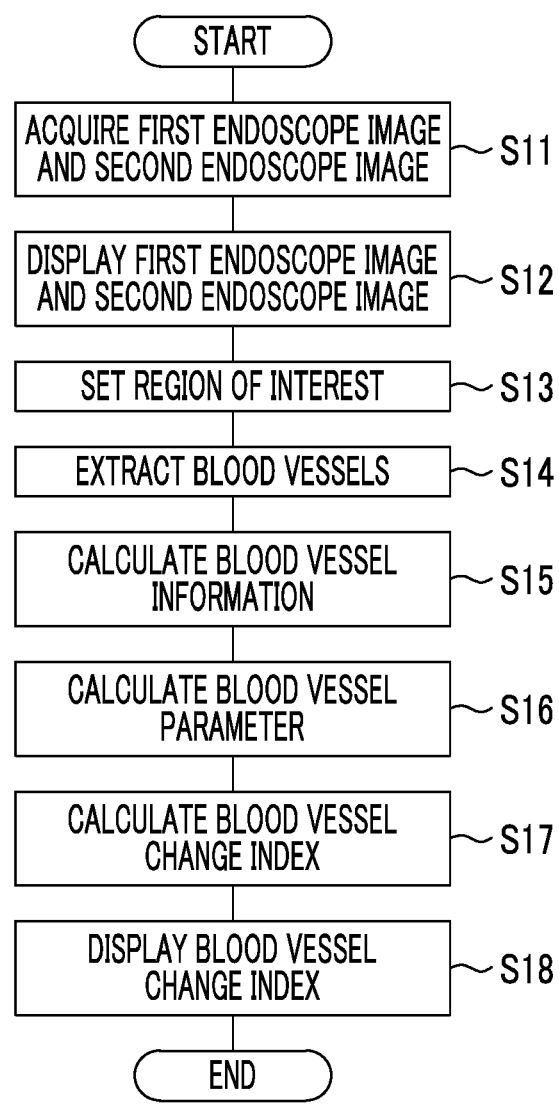
FIG. 6 is a flowchart showing the operation of the image processing apparatus.

Next, the flow of the operation of the image processing apparatus 65 will be described with reference to a flowchart shown in FIG. 6. First, according to the input operation of the input device 87, the image processing apparatus 65 acquires the first endoscope image 101 and the second endoscope image 102 from the storage 64 using the image acquisition unit 81 (S11), and displays these images on the monitor 88 (S12). The image processing apparatus 65 displays the first endoscope image 101 whose imaging time is relatively earlier, between the acquired first endoscope image 101 and second endoscope image 102, on the subwindow 116, and displays the second endoscope image 102 whose imaging time is relatively later on the main window 115.

Figure 7:
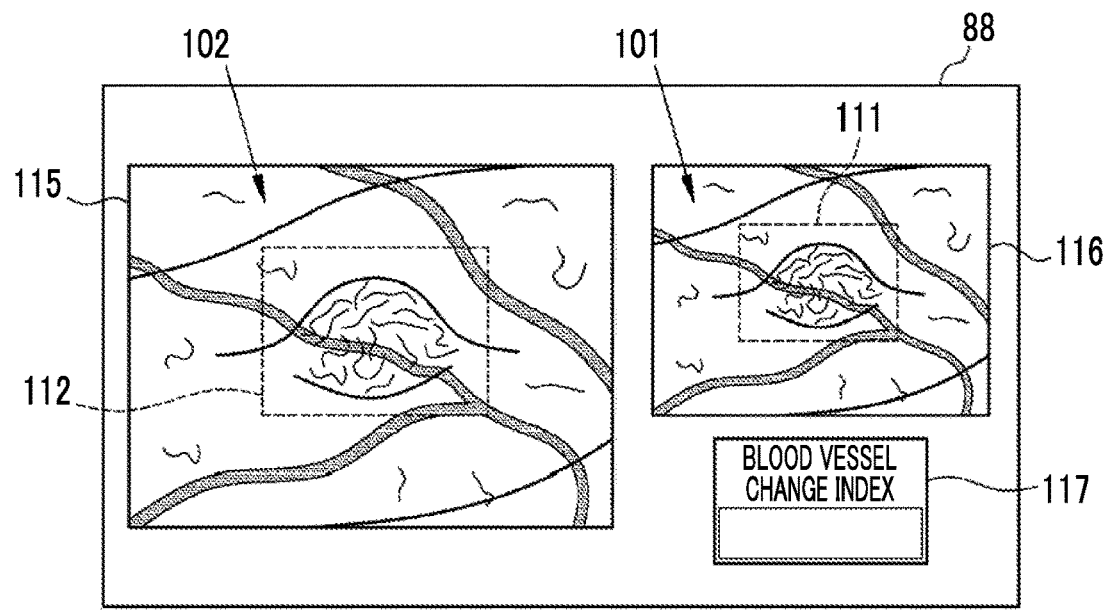
FIG. 7 is an explanatory diagram showing a method of setting a region of interest.

In a case where the selected first endoscope image 101 and second endoscope image 102 are displayed on the monitor 88, a doctor operates the input device 87 to set a region of interest in each of the first endoscope image 101 and the second endoscope image 102 (S13). For example, as shown in FIG. 7, there is an attention portion, which requires diagnosis of whether or not there is a lesion (or the degree of progress of a lesion or the like), in the vicinity of the approximate center of the second endoscope image 102 of the main window 115. Therefore, the doctor operates the input device 87 to set a region of interest (hereinafter, referred to as a second region of interest) 112 including the attention portion in the second endoscope image 102. For the first endoscope image 101 of the subwindow 116, a region of interest (hereinafter, referred to as a first region of interest) 111 including an attention portion, which is the same as (or corresponds to) the attention portion of the second endoscope image 102, is set.

Figure 8:
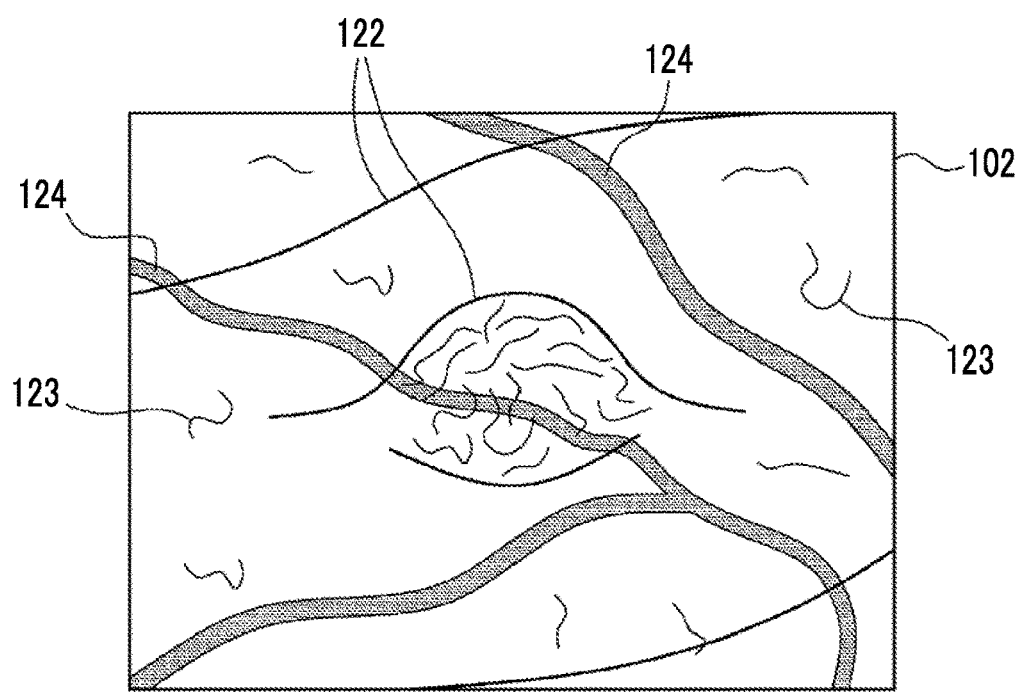
FIG. 8 is a schematic diagram of a second endoscope image.
Figure 9:
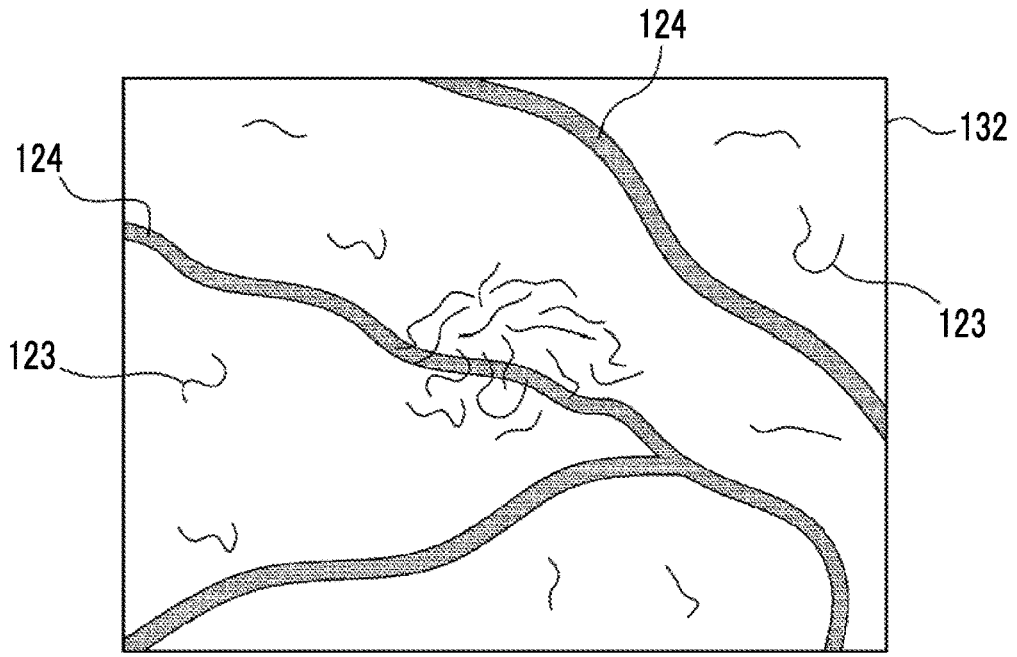
FIG. 9 is a second blood vessel image showing an extracted second blood vessel.

On the other hand, the blood vessel extraction unit 82 extracts the first blood vessel from the first endoscope image 101, and extracts the second blood vessel from the second endoscope image 102 (S14). As shown in FIG. 8, the second endoscope image 102 is a special observation image in which blood vessels are emphasized by color. For example, not only can the shape 122 of the surface of the mucous membrane of the observation target be observed, but also a thin surface layer blood vessel 123 located relatively close to the surface of the mucous membrane is expressed by a magenta type color and a thick middle deep layer blood vessel 124 located at a relatively deep position under the mucous membrane is expressed by a cyan type color so as to be emphasized. In the case of the second endoscope image 102, the blood vessel extraction unit 82 extracts the surface layer blood vessel 123 and the middle deep layer blood vessel 124 as second blood vessels like a second blood vessel image 132 schematically shown in FIG. 9. The blood vessel extraction unit 82 extracts a first blood vessel from the first endoscope image 101 in the same manner as in the extraction of the second blood vessel from the second endoscope image 102.

In a case where the first blood vessel is extracted from the first endoscope image 101 by the blood vessel extraction unit 82 as described above, the blood vessel information calculation unit 83 calculates the first blood vessel information regarding the first blood vessel for each pixel of the first endoscope image 101 and calculates the statistic of the first region of interest 111, thereby calculating the first blood vessel information of the first region of interest 111 (S15). Similarly, in a case where the second blood vessel is extracted from the second endoscope image 102 by the blood vessel extraction unit 82, the blood vessel information calculation unit 83 calculates the second blood vessel information regarding the second blood vessel for each pixel of the second endoscope image 102 and calculates the statistic of the second region of interest 112, thereby calculating the second blood vessel information of the second region of interest 112 (S15). As described above, the blood vessel information calculation unit 83 calculates a plurality of pieces of first blood vessel information regarding the first blood vessel and a plurality of pieces of second blood vessel information regarding the second blood vessel.

In a case where the plurality of pieces of first blood vessel information regarding the first blood vessel are calculated by the blood vessel information calculation unit 83, the blood vessel parameter calculation unit 84 calculates the first blood vessel parameter P1 by calculation using the plurality of pieces of first blood vessel information (S16). Similarly, in a case where the plurality of pieces of second blood vessel information regarding the second blood vessel are calculated by the blood vessel information calculation unit 83, the blood vessel parameter calculation unit 84 calculates the second blood vessel parameter P2 by calculation using the plurality of pieces of second blood vessel information (S16).

In a case where the first blood vessel parameter P1 and the second blood vessel parameter P2 are calculated by the blood vessel parameter calculation unit 84, the blood vessel change index calculation unit 85 calculates the blood vessel change index 108 indicating a temporal change of the blood vessel of the observation target using the first blood vessel parameter P1 and the second blood vessel parameter P2 (S17). The image processing apparatus 65 displays the blood vessel change index 108 calculated by the blood vessel change index calculation unit 85 in the blood vessel change index display portion 117 of the monitor 88 (refer to FIG. 5). The image processing apparatus 65 automatically performs those other than the selection of the first endoscope image 101 and the second endoscope image 102 and the setting of the first region of interest 111 and the second region of interest 112. For this reason, in a case where the doctor using the image processing apparatus 65 selects two endoscope images from the storage 64 and sets a region of interest in each of the selected endoscope images on the monitor 88, the blood vessel change index 108 is automatically displayed in the blood vessel change index display portion 117.

As described above, the image processing apparatus 65 assists the doctor's diagnosis not only by calculating various kinds of blood vessel information but also by calculating the first blood vessel parameter P1 and the second blood vessel parameter P2 by calculation using a plurality of pieces of blood vessel information and calculating the blood vessel change index 108 using the first blood vessel parameter P1 and the second blood vessel parameter P2.

The first blood vessel parameter P1 serves as a guide for diagnosis of the observation target at the imaging time T1 of the first endoscope image 101, and the second blood vessel parameter P2 serves as a guide for diagnosis of the observation target at the imaging time T2 of the second endoscope image 102. In addition, since the blood vessel change index 108 is an index indicating how these blood vessel parameters change with time, it is particularly useful for improving the accuracy of diagnosis. According to the blood vessel change index 108, for example, not only a mere increase/decrease in the blood vessel parameter but also the degree of increase/decrease in the blood vessel parameter can be quantitatively grasped to perform diagnosis. Even in a case where diagnosis is difficult due to lack of accuracy due to diagnosis based only on the absolute values of the first blood vessel parameter P1 and the second blood vessel parameter P2, accurate diagnosis may be able to be made by observing a change in the blood vessel parameter through the blood vessel change index 108.

According to the blood vessel change index 108, it is possible to predict how the blood vessel of the observation target will change in the future. Such a prediction was based on the experience of a doctor in the past. However, in the case of the image processing apparatus 65, the blood vessel change index 108 assists accurate prediction. Therefore, any doctor can make a prediction closer to that of a skilled doctor.

Second Embodiment

Figure 10:
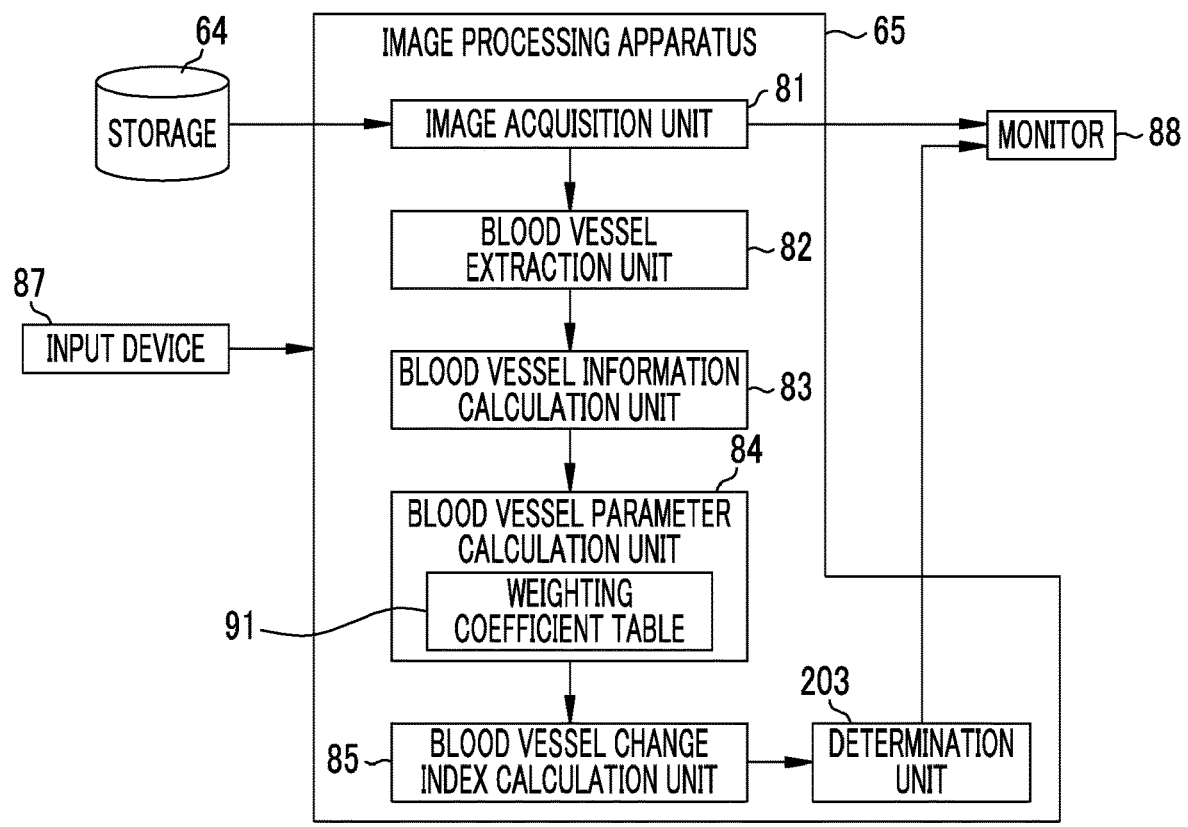
FIG. 10 is a block diagram of an image processing apparatus of a second embodiment.

In the first embodiment described above, the blood vessel change index 108 is displayed on the monitor 88. However, as shown in FIG. 10, a determination unit 203 for determining the state of the mucous membrane of the observation target using a blood vessel change index may be provided in the image processing apparatus 65, and the determination result of the determination unit 203 may be displayed 108, instead of the blood vessel change index, on the monitor 88. The "state of the mucous membrane" of the observation target is a comprehensive status as the entire mucous membrane including blood vessels. For example, the "state of the mucous membrane" of the observation target is "normal", "adenoma" (suspected of adenoma), "cancer" (suspected of cancer), and the like.

The determination unit 203 acquires the blood vessel change index 108 from the blood vessel change index calculation unit 85, and determines the state of the mucous membrane of the observation target based on the blood vessel change index 108 or by performing further calculation using the blood vessel change index 108.

Figure 11:
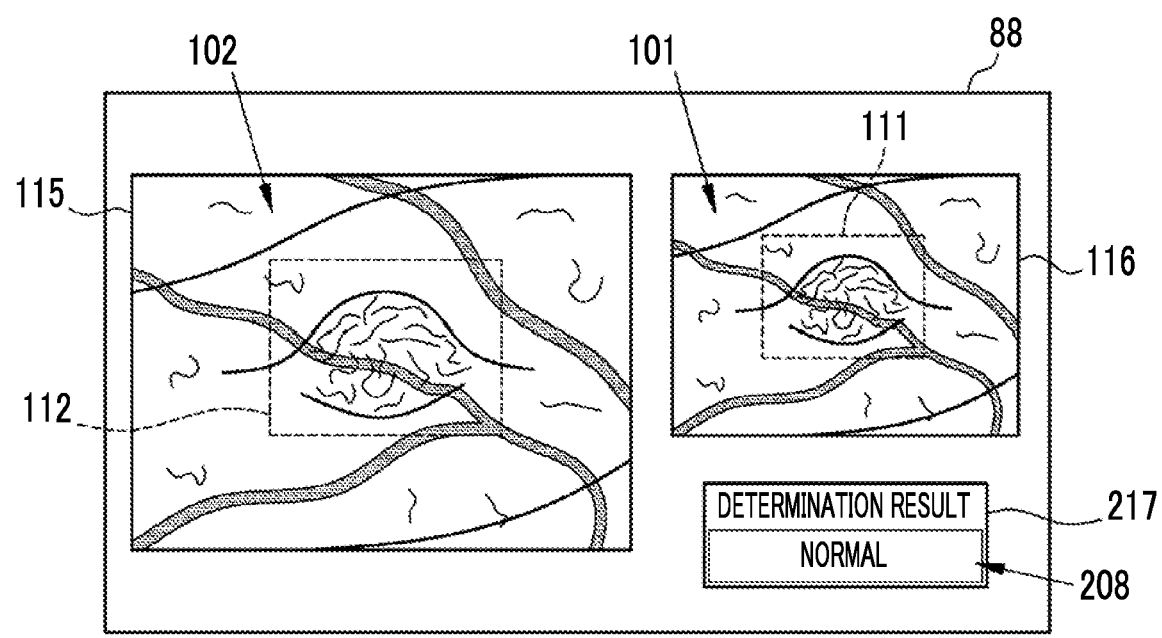
FIG. 11 is a display screen of a monitor for displaying the determination result of a determination unit.

For example, it is assumed that a weighting coefficient used for calculating a blood vessel parameter is set as a balance for determining the state of the mucous membrane to one of three kinds of states (normal, adenoma, and cancer). In this case, the determination unit 203 determines that the state of the mucosa of the observation target is "normal" in a case where the change in the second blood vessel parameter P2 with respect to the first blood vessel parameter P1 is small and the blood vessel change index 108 is equal to or less than a first threshold value TH1. In a case where the change in the second blood vessel parameter P2 with respect to the first blood vessel parameter P1 is moderate and the blood vessel change index 108 is greater than the first threshold value TH1 and equal to or less than a second threshold value TH2, the determination unit 203 determines that the state of the mucosa of the observation target is "adenoma". In a case where the change in the second blood vessel parameter P2 with respect to the first blood vessel parameter P1 is large and the blood vessel change index 108 is greater than the second threshold value TH2, the determination unit 203 determines that the state of the mucosa of the observation target is "cancer". Then, as shown in FIG. 11, instead of the blood vessel change index display portion 117, a determination result display portion 217 is provided on the display screen of the monitor 88 to display a determination result 208 of the determination unit 203 described above.

As described above, by providing the determination unit 203 in the image processing apparatus 65, determining the state of the mucous membrane of the observation target using the blood vessel change index 108, and displaying the determination result 208, it is possible to assist the diagnosis so as to be easily understood in a more straightforward way than in a case where the blood vessel change index 108 is displayed.

It is desirable that the determination unit 203 determines the state of the mucous membrane to three or more states including normal, adenoma, and cancer. In particular, in the case of determining the state of the mucous membrane of the large intestine, it is preferable to determine the state of the mucous membrane of the large intestine to any state including normal, hyperplastic polyp (HP), sessile serrated adenoma/Polyp (SSA/P), traditional serrated adenoma (TSA), laterally spreading tumor (LST), and cancer. In a case where the determination result of the determination unit 203 is subdivided as described above, it is preferable that the determination unit 203 uses a blood vessel parameter or blood vessel information in addition to the blood vessel change index 108. Conventionally, a hyperplastic polyp was thought to have low risk of canceration and does not need to be treated. In recent years, however, an example in which an SSA/P analogous to a hyperplastic polyp is cancerated has also been discovered. In particular, it is becoming important to differentiate between the hyperplastic polyp and the SSA/P. On the other hand, it is known that an SSA/P is likely to be formed in a case where the middle deep layer blood vessel 124 traverses under the thickened mucous membrane thought to be a hyperplastic polyp or SSA/P. By using the blood vessel change index 108, the determination unit 203 can differentiate between the hyperplastic polyp and the SSA/P. However, by using the blood vessel change index 108 and the blood vessel parameter or blood vessel information (thickness and length of a blood vessel) in combination, it is possible to differentiate between the hyperplastic polyp and the SSA/P with a higher probability.

In a case where the state of the mucous membrane of the observation target is cancer, it is preferable that the determination unit 203 further determines the stage of cancer using the blood vessel change index 108 or the blood vessel parameter (the first blood vessel parameter P1 or the second blood vessel parameter P2). Then, it is preferable to display the stage of the cancer determined by the determination unit 203 in the determination result display portion 217. In this manner, in a case where the state of the mucous membrane of the observation target is determined to be cancer, the stage is further determined and the result is displayed on the monitor 88, so that the diagnosis can be more finely assisted. In a case where the state of the mucous membrane of the observation target is cancer and the stage of the cancer is further determined, the stage of the cancer may be determined by combining the blood vessel information with the blood vessel change index 108 or the blood vessel parameter (the first blood vessel parameter P1 or the second blood vessel parameter P2).

In the second embodiment described above, the determination result of the determination unit 203 is displayed on the monitor 88. However, instead of displaying the determination result itself of the determination unit 203 on the monitor 88, a warning may be displayed based on the determination result of the determination unit 203. For example, in a case where the determination result of the determination unit 203 is "cancer", it is preferable to display a warning message based on the determination result, such as "there is a possibility of cancer", in the determination result display portion 217.

Third Embodiment

Figure 12:
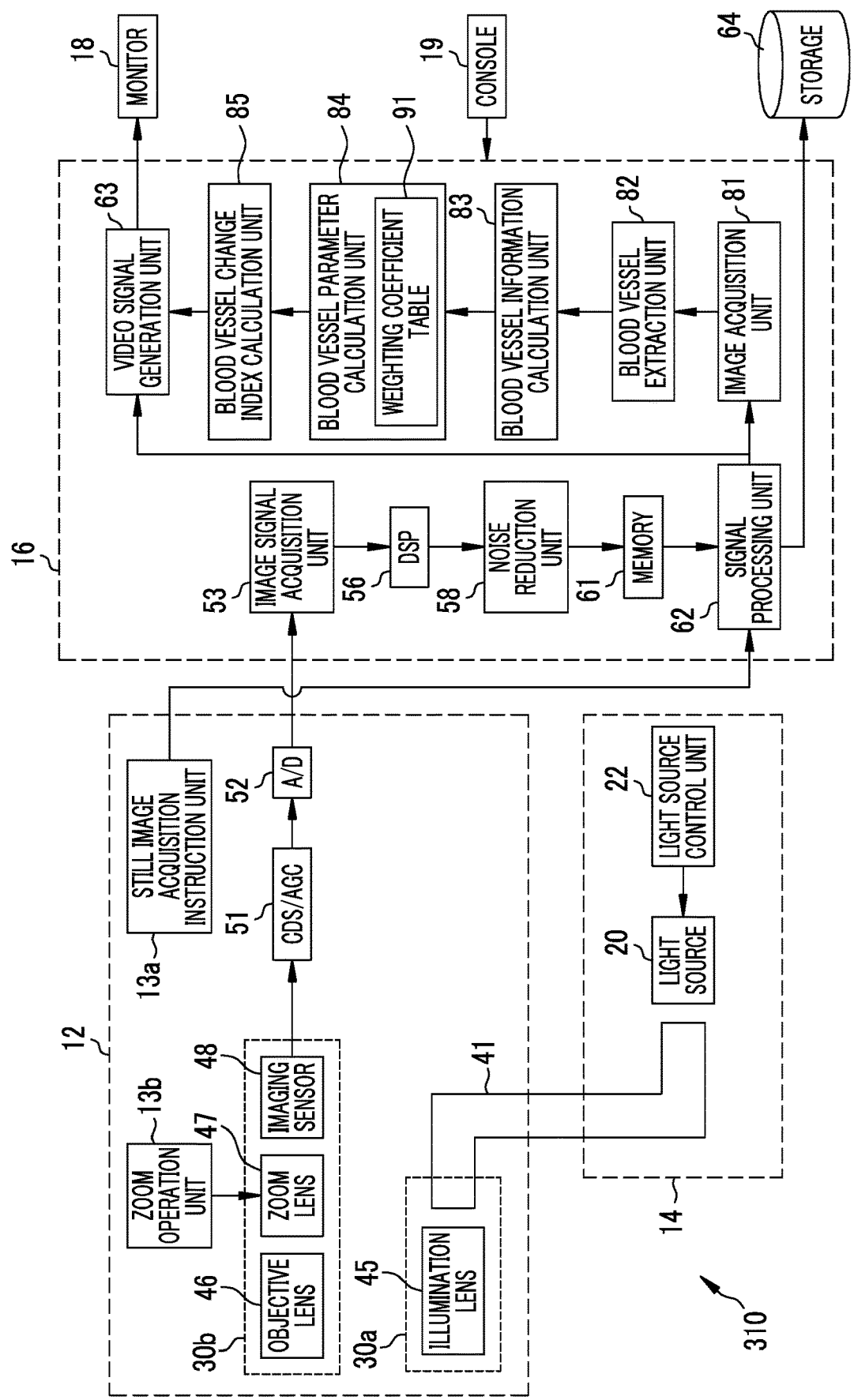
FIG. 12 is a block diagram of an endoscope system of a third embodiment.

In the first and second embodiments described above, the endoscope system 10 stores an endoscope image in the storage 64, and the image processing apparatus 65 acquires the endoscope image from the storage 64 later to calculate a blood vessel parameter. However, the endoscope system 10 may calculate the blood vessel change index 108 almost in real time while observing the observation target. In this case, as in an endoscope system 310 shown in FIG. 12, the image acquisition unit 81, the blood vessel extraction unit 82, the blood vessel information calculation unit 83, the blood vessel parameter calculation unit 84, and the blood vessel change index calculation unit 85 are provided in the processor device 16. The configuration of the endoscope 12 or the light source device 14 is the same as that of the endoscope system 10 of the first embodiment.

In a case where each unit of the image processing apparatus 65 is provided in the processor device 16 as described above, the image acquisition unit 81 can directly acquire the endoscope image generated by the signal processing unit 62 from the signal processing unit 62 without passing through the storage 64. Therefore, the image acquisition unit 81 temporarily holds at least two or more endoscope images generated in a case where, for example, a still image acquisition instruction is input, and inputs the endoscope images to the blood vessel extraction unit 82 as the first endoscope image 101 and the second endoscope image 102 of the first embodiment.

As in the case of using the input device 87 in the first embodiment, which endoscope images among the plurality of endoscope images temporarily held by the image acquisition unit 81 are to be used as the first endoscope image 101 and the second endoscope image 102 of the first embodiment can be selected by the doctor using the console 19 of the endoscope system 310. For example, among the plurality of endoscope images temporarily held by the image acquisition unit 81, the oldest endoscope image (endoscope image having the earliest imaging time) is used as the first endoscope image 101, and the newest endoscope image (endoscope image having the latest imaging time) is used as the second endoscope image 102. In this manner, endoscope images to be used as the first endoscope image 101 and the second endoscope image 102 can be set in advance by using the console 19.

The operations of the blood vessel extraction unit 82, the blood vessel information calculation unit 83, the blood vessel parameter calculation unit 84, and the blood vessel change index calculation unit 85 other than the image acquisition unit 81 are the same as those in the endoscope system 10 of the first embodiment. The blood vessel change index 108 calculated by the blood vessel change index calculation unit 85 is displayed on the monitor 18 of the endoscope system 310 through the video signal generation unit 63. The display method of the blood vessel change index 108 is the same as in the first embodiment.

As described above, in a case where each unit of the image processing apparatus 65 is provided in the processor device 16, the processor device 16 also functions as the image processing apparatus 65. Therefore, in the endoscope system 310, since the blood vessel change index 108 is calculated while observing the observation target, it is possible to assist the diagnosis almost in real time. The endoscope system 310 is suitable for observing the action in the case of administering a medicine to the observation target or performing an operation on the observation target.

In the third embodiment described above, the image acquisition unit 81 directly acquires the endoscope image generated by the signal processing unit 62. However, instead of directly acquiring the endoscope image from the signal processing unit 62, the first endoscope image 101 and the second endoscope image 102 may be acquired from the storage 64 as in the first embodiment or the like. In particular, as the first endoscope image 101, an endoscope image obtained by the past examination that is stored in the storage 64 may be used. In a case where an endoscope image obtained by the past examination is used as the first endoscope image 101, it is possible to know the change of the current observation target with respect to the past observation target in real time during the current examination by the blood vessel change index 108.

In the third embodiment described above, the endoscope image acquired by the image acquisition unit 81 from the signal processing unit 62 is an endoscope image generated in a case where a still image acquisition instruction is input. However, the blood vessel change index 108 may be calculated regardless of the still image acquisition instruction. In this case, it is preferable that the setting of a region of interest, extraction of a blood vessel, calculation of blood vessel information, calculation of a blood vessel parameter, and calculation of the blood vessel change index 108 are automatically performed at predetermined time intervals. The time interval for calculating the blood vessel change index 108 can be arbitrarily set by the doctor.

Fourth Embodiment

In the first to third embodiments described above, two endoscope images of the first endoscope image 101 and the second endoscope image 102 are used for the calculation of the blood vessel change index 108. However, the blood vessel change index 108 may be calculated using three or more endoscope images.

Figure 13:
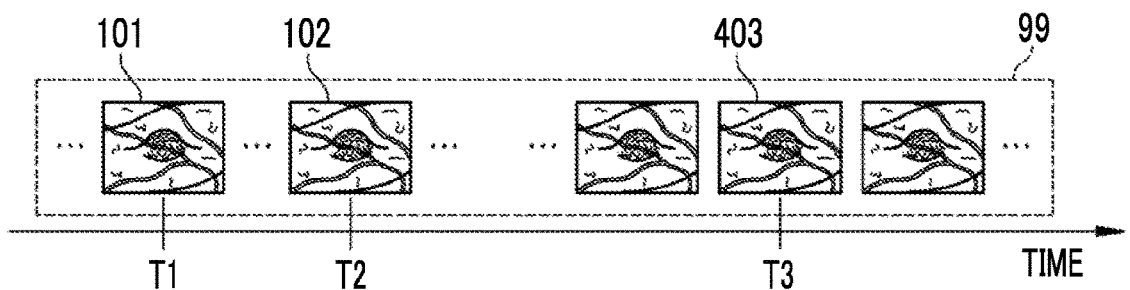
FIG. 13 is an explanatory diagram showing a third endoscope image used in a fourth embodiment.

For example, as shown in FIG. 13, the image acquisition unit 81 acquires not only the first endoscope image 101 and the second endoscope image 102 but also a third endoscope image 403, which is obtained by imaging the observation target after the second endoscope image 102, among the plurality of endoscope images 99 stored in the storage 64. In a case where the imaging time T1 of the first endoscope image 101, the imaging time T2 of the second endoscope image 102, and the imaging time T3 of the third endoscope image 403 are compared, T1<T2<T3 is satisfied.

Figure 14:
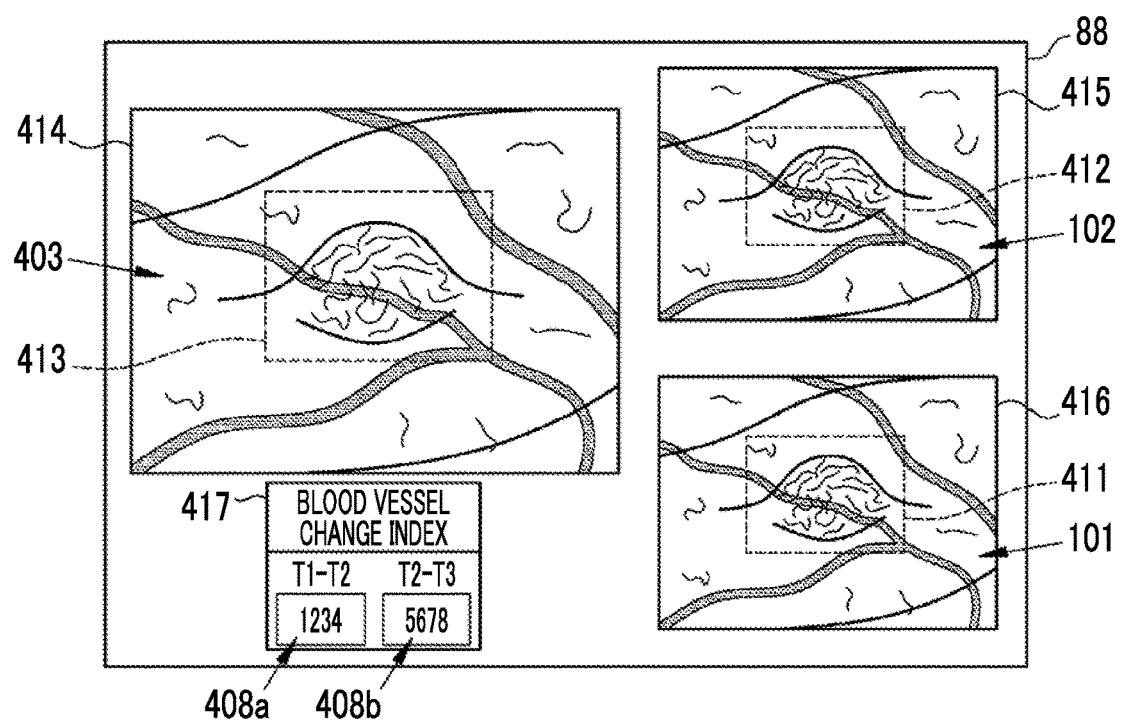
FIG. 14 is a display screen of a monitor in the fourth embodiment.

In this case, as shown in FIG. 14, display regions of three endoscope images of a main window 414, a first subwindow 415, and a second subwindow 416 are provided on the monitor 88. Then, in a case where the image acquisition unit 81 acquires the first endoscope image 101, the second endoscope image 102, and the third endoscope image 403, the image processing apparatus 65 displays the third endoscope image 403 obtained by imaging the observation target relatively most recently in the main window 414, displays the second endoscope image 102 obtained by secondly imaging the observation target in the first subwindow 415, and the first endoscope image 101 obtained by imaging the observation target relatively earliest in the second subwindow 416.

In a case where the image processing apparatus 65 displays the first endoscope image 101, the second endoscope image 102, and the third endoscope image 403 on the monitor 88, the doctor sets a region of interest corresponding to each of the endoscope images in the same manner as in the first embodiment and the like. That is, first, a region of interest (hereinafter, referred to as a third region of interest) 413 is set in the third endoscope image 403, and a second region of interest 412 including an attention portion, which is the same as (or corresponds to) the attention portion included in the third region of interest 413, is set in the second endoscope image 102. Similarly for the first endoscope image 101, the first region of interest 411 is set.

In a case where a region of interest is set in each of the first endoscope image 101, the second endoscope image 102, and the third endoscope image 403 as described above, the blood vessel extraction unit 82 extracts a first blood vessel from the first endoscope image 101 and extracts a second blood vessel from the second endoscope image 102. Then, a blood vessel of the observation target is extracted from the third endoscope image 403 in the same manner as extracting the first blood vessel from the first endoscope image 101 and extracting the second blood vessel from the second endoscope image 102. Hereinafter, the blood vessel extracted from the third endoscope image 403 is referred to as a third blood vessel.

Then, the blood vessel information calculation unit 83 calculates a plurality of pieces of first blood vessel information for the first blood vessel, calculates a plurality of pieces of second blood vessel information for the second blood vessel, and calculates a plurality of pieces of the same blood vessel information (hereinafter, referred to as third blood vessel information) as the first blood vessel information and the second blood vessel information for the third blood vessel extracted from the third endoscope image 403 in the same manner as calculating a plurality of pieces of first blood vessel information for the first blood vessel (or calculating a plurality of pieces of second blood vessel information for the second blood vessel). The plurality of pieces of first blood vessel information, the plurality of pieces of second blood vessel information, and the plurality of pieces of third blood vessel information newly calculated in the present embodiment are the same in kind (combination of kinds).

The blood vessel parameter calculation unit 84 calculates the first blood vessel parameter P1 by calculation using a plurality of pieces of first blood vessel information and calculates the second blood vessel parameter P2 by calculation using a plurality of pieces of second blood vessel information in the same manner as in the first embodiment. In the present embodiment, the blood vessel parameter calculation unit 84 calculates a blood vessel parameter relevant to the third blood vessel (hereinafter, referred to as a third blood vessel parameter P3) by calculation using a plurality of pieces of third blood vessel information, in the same manner as calculating the first blood vessel parameter P1 and the second blood vessel parameter P2. The calculation for calculating the third blood vessel parameter P3 from the plurality of pieces of third blood vessel information is the same as the calculation in the case of calculating the first blood vessel parameter P1 and the second blood vessel parameter P2.

In a case where the first blood vessel parameter P1, the second blood vessel parameter P2, and the third blood vessel parameter P3 are calculated as described above, the blood vessel change index calculation unit 85 calculates blood vessel change indices 408a and 408b using these blood vessel parameters and displays the blood vessel change indices 408a and 408b in a blood vessel change index display portion 417 of the monitor 88 (refer to FIG. 14). In the first embodiment, since there are only two blood vessel parameters of the first blood vessel parameter P1 and the second blood vessel parameter P2, the blood vessel change index calculation unit 85 calculates a change in the second blood vessel parameter P2 with respect to the first blood vessel parameter P1, and sets the value as the blood vessel change index 108. In the present embodiment, however, there are three blood vessel parameters of the first blood vessel parameter P1, the second blood vessel parameter P2, and the third blood vessel parameter P3. Therefore, the blood vessel change index calculation unit 85 calculates the blood vessel change index 108 inductively in order of the imaging times of the first to third endoscope images 101, 102, 403, for example. Specifically, a change (difference Δ or the like) of the second blood vessel parameter P2 with respect to the first blood vessel parameter P1 is calculated, and a change in the third blood vessel parameter P3 with respect to the second blood vessel parameter P2 is calculated. The change in the second blood vessel parameter P2 with respect to the first blood vessel parameter P1 is the blood vessel change index 408a between the imaging times T1 and T2, and the change in the third blood vessel parameter P3 with respect to the second blood vessel parameter P2 is the blood vessel change index 408b between the imaging times T2 and T3.

In the fourth embodiment described above, the blood vessel change index calculation unit 85 calculates the blood vessel change index 108 inductively in order of the imaging times of the first to third endoscope images 101, 102, and 403. However, the blood vessel change index calculation unit 85 can also calculate the blood vessel change index by setting any of the imaging times of the first to third endoscope images 101, 102, and 403 as the reference time. For example, the imaging time T1 of the first endoscope image 101 can be set as the reference time, and the change in the second blood vessel parameter P2 with respect to the first blood vessel parameter P1 (change in the blood vessel parameter between the imaging times T1 and T2) and the change in the third blood vessel parameter P3 with respect to the first blood vessel parameter P1 (change in the blood vessel parameter between the imaging times T1 and T3) can be calculated as blood vessel change indices. Needless to say, the imaging time T2 of the second endoscope image 102 or the imaging time T3 of the third endoscope image 403 may be set as the reference time.

In the fourth embodiment described above, three endoscope images of the first endoscope image 101, the second endoscope image 102, and the third endoscope image 403, are used. However, also in the case of using four or more endoscope images, the blood vessel change index 408 can be calculated in the same manner as in the fourth embodiment. How many endoscope images are to be used to calculate the blood vessel change index 408 can be arbitrarily set by the doctor. For example, setting such as using the latest endoscope image or using the past five endoscope images is possible. Such setting can be changed depending on the type of the blood vessel change index 408 (or the type of blood vessel parameter).

Figure 15:
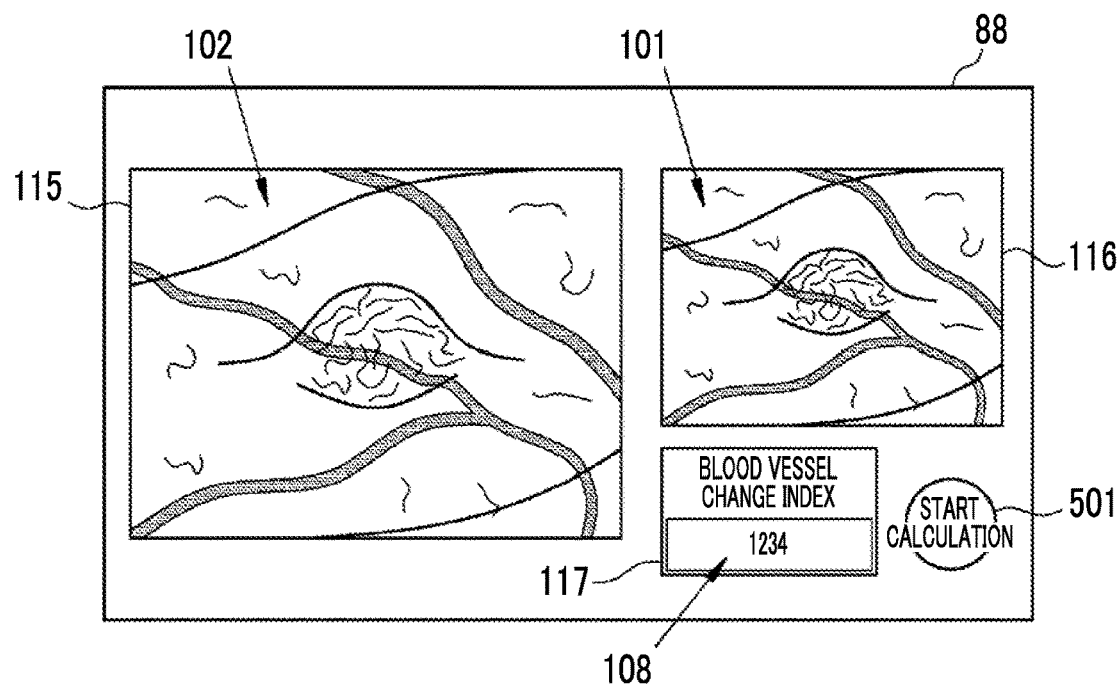
FIG. 15 is a display screen of a monitor on which a calculation start button is provided.

In the first to fourth embodiments described above, the blood vessel change index 108 (in the fourth embodiment, the blood vessel change index 408) is calculated by setting a region of interest in an endoscope image displayed on the monitor 88, such as the first endoscope image 101. That is, in the first to fourth embodiments, the trigger for starting the calculation of the blood vessel change index 108 is the setting of a region of interest. Therefore, in a case where a region of interest is not set or a case where the entire endoscope image displayed on the monitor 88 is set as a region of interest, for example, as shown in FIG. 15, a calculation start button 501 for instructing to start the calculation of the blood vessel change index 108 is displayed on the monitor 88, and the calculation of the blood vessel change index 108 is started with the operation of the calculation start button 501 by the input device 87 (in the case of the third embodiment, the console 19) as a trigger. In a case where the selection of an endoscope image used for the calculation of the blood vessel change index 108, such as the first endoscope image 101, is completed (or in a case where a predetermined time has passed after the selection), the calculation of the blood vessel change index 108 may be automatically started.

In the first to fourth embodiments described above, one region of interest is set for each endoscope image such as the first endoscope image 101 displayed on the monitor 88. However, a plurality of regions of interest may be set for each endoscope image such as the first endoscope image 101 displayed on the monitor 88. For example, each region obtained by dividing the entire endoscope image into meshes can be set as a region of interest, and the blood vessel change index 108 can be calculated in each region of interest. In addition, the doctor may set an arbitrary number of regions of interest at arbitrary places.

In the first to fourth embodiments described above, one blood vessel change index 108 is calculated. However, a plurality of blood vessel change indices may be calculated. In this case, for example, in addition to the weighting coefficient table 91, a second weighting coefficient table in which different weighting coefficients from those of the weighting coefficient table 91 are stored is prepared in advance. Then, the blood vessel parameter calculation unit 84 calculates the first blood vessel parameter P1 and the second blood vessel parameter P2 using the weighting coefficients of the weighting coefficient table 91, and calculates a first blood vessel parameter Q1 relevant to the first blood vessel that is different from the first blood vessel parameter P1 and a second blood vessel parameter Q2 relevant to the second blood vessel that is different from the second blood vessel parameter P2 by using the weighting coefficients of the second weighting coefficient table. Thereafter, the blood vessel change index calculation unit 85 calculates the blood vessel change index 108 (first blood vessel change index) using the first blood vessel parameter P1 and the second blood vessel parameter P2, and calculates a second blood vessel change index using the first blood vessel parameter Q1 and the second blood vessel parameter Q2. In this manner, by calculating a plurality of types of blood vessel change indices and displaying these on the monitor 88, the doctor can diagnose the observation target simultaneously from a plurality of viewpoints. The same is true for a case where three or more endoscope images are used.

In a case where a plurality of types of blood vessel change indices are calculated as described above, the image processing apparatus 65 (or the endoscope system 310 of the third embodiment) can display all the calculated blood vessel change indices on the monitor 88. However, it is preferable to preferentially display a blood vessel change index (for example, a blood vessel change index having a high change rate) to be most noticed. The same is true for a case where there are a plurality of blood vessel change indices by setting a region of interest at a plurality of places and calculating the blood vessel change index at each place. In addition, the same is true for a case where the determination result of the determination unit 203 is displayed, and a determination result showing a possibility of abnormality, such as adenoma, may be displayed on the monitor 88, and the display of a determination result showing a normal state may be omitted.

In the first to fourth embodiments described above, the first endoscope image 101 and the second endoscope image 102 are selected and acquired from a plurality of endoscope images 99 stored in the storage 64. However, these may be selected in any order. The second endoscope image 102 may be selected, and an endoscope image having a similar appearance of the observation target to that of the second endoscope image 102 may be selected as the first endoscope image 101 while observing the second endoscope image 102 on the monitor 88. Conversely, the second endoscope image 102 may be selected after selecting the first endoscope image 101.

Figure 16:
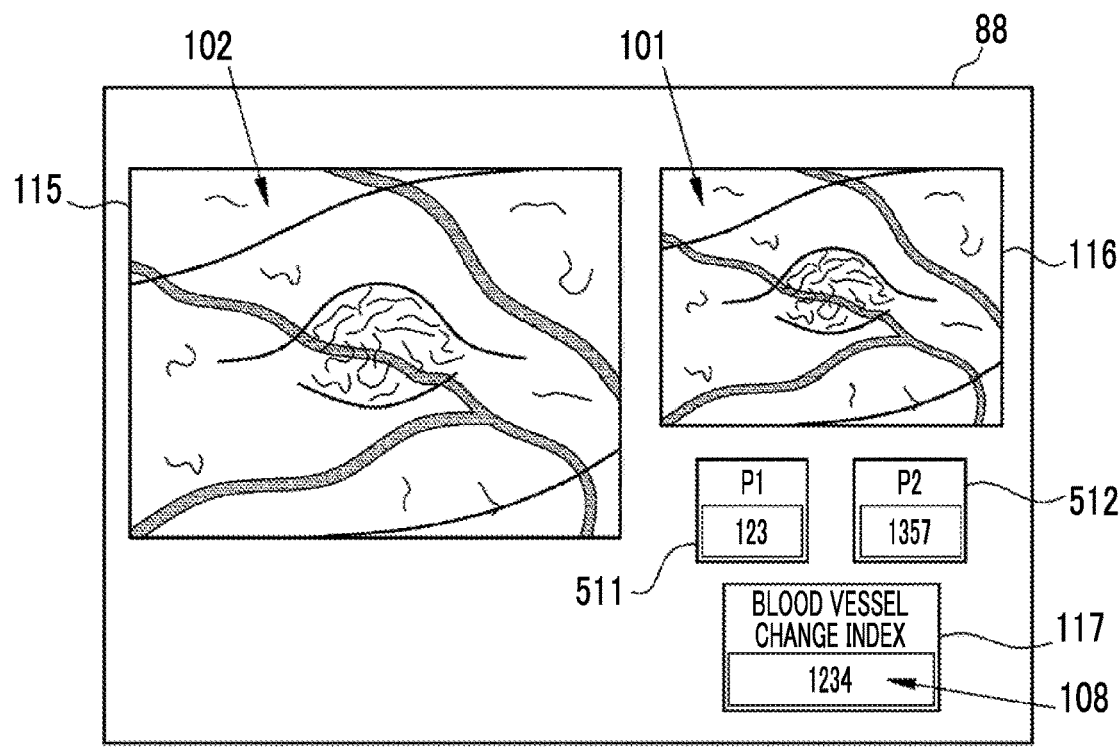
FIG. 16 is a display screen of a monitor for displaying a blood vessel parameter.

In the first to fourth embodiments described above, the blood vessel change index 108 (in the fourth embodiment, the blood vessel change index 408) or the determination result of the determination unit 203 is displayed on the monitor 88 (in the third embodiment, the monitor 18). However, as shown in FIG. 16, it is preferable to display not only the blood vessel change index 108 or the determination result of the determination unit 203 but also the calculated blood vessel parameter, such as the first blood vessel parameter P1 or the second blood vessel parameter P2, on the monitor 88. FIG. 16 shows that a first blood vessel parameter display portion 511 for displaying the first blood vessel parameter P1 and a second blood vessel parameter display portion 512 for displaying the second blood vessel parameter P2 are provided and each value of the first blood vessel parameter P1 and the second blood vessel parameter P2 is displayed in addition to the blood vessel change index 108. The same is true for a case of displaying the determination result of the determination unit 203 or a case of displaying both the blood vessel change index 108 and the determination result on the monitor 88.

Weighting coefficients used for calculating blood vessel parameters or blood vessel information, such as the first blood vessel information or the second blood vessel information, may be displayed on the monitor 88. In a case where the weighting coefficient used for calculating the blood vessel parameter is displayed on the monitor 88, it is preferable to be able to change the weighting coefficient by inputting a numerical value on the monitor 88 as well as simply displaying the weighting coefficient. In this manner, by displaying blood vessel parameters and the like in addition to the blood vessel change index 108 or the determination result of the determination unit 203, the doctor can easily grasp the meaning of the blood vessel change index 108 and the basis of the determination. In addition, by displaying the weighting coefficient and making the weighting coefficient changeable, it is possible to provide a method of adjusting the method of calculating blood vessel parameters based on the experience of the doctor.

For example, a "check mode" for additionally displaying blood vessel parameters and the like may be provided, and the blood vessel parameters and the like may be displayed in addition to the blood vessel change index 108 in a case where the check mode is set using the input device 87 or the like (the operation unit 12b or the console 19 in the case of the endoscope system 310, a foot pedal (not shown), and the like).

Figure 17:
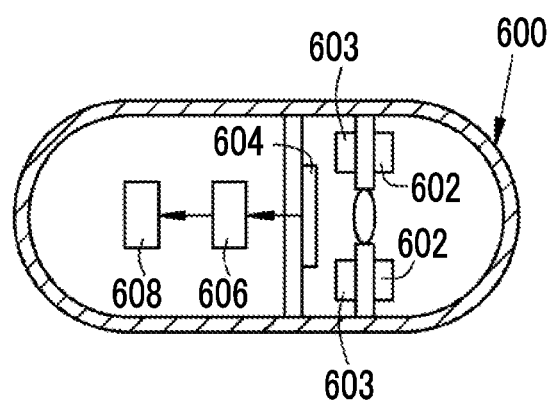
FIG. 17 is a schematic diagram of a capsule endoscope.

In the first to fourth embodiments described above, the present invention is implemented by the endoscope system 10 (or the endoscope system 310) that performs observation by inserting the endoscope 12, in which the imaging sensor 48 is provided, into the subject. However, the present invention is also suitable for a capsule endoscope system. For example, as shown in FIG. 17, a capsule endoscope system includes at least a capsule endoscope 600 and a processor device (not shown). The capsule endoscope 600 includes a light source 602, a light source control unit 603, an imaging sensor 604, an image signal acquisition processing unit 606, and a transmitting and receiving antenna 608. The light source 602 is configured similarly to the light source 20 of the endoscope system 10, and emits illumination light under the control of the light source control unit 603. The image signal acquisition processing unit 606 functions as the image signal acquisition unit 53, the DSP 56, the noise reduction unit 58, and the signal processing unit 62. The processor device of the capsule endoscope system is configured similarly to the processor device 16 of the endoscope system 310, and also functions as the image processing apparatus 65.

EXPLANATION OF REFERENCES

10: endoscope system
12: endoscope
12a: insertion part
12b: operation unit
12c: bending portion
12d: distal end portion
12e: angle knob
13a: still image acquisition instruction unit
13b: zoom operation unit
14: light source device
16: processor device
18: monitor
19: console
20: light source
22: light source control unit
30a: illumination optical system
30b: imaging optical system
41: light guide
45: illumination lens
46: objective lens
47: zoom lens
48: imaging sensor
51: CDS/AGC circuit
52: AD converter
53: image signal acquisition unit
56: DSP
58: noise reduction unit
61: memory
62: signal processing unit
63: video signal generation unit
64: storage
65: image processing apparatus
81: image acquisition unit
82: blood vessel extraction unit
83: blood vessel information calculation unit
84: blood vessel parameter calculation unit
85: blood vessel change index calculation unit
87: input device
88: monitor
91: coefficient table
99: endoscope image
101: first endoscope image 102: second endoscope image
108: blood vessel change index
111: first region of interest
112: second region of interest
115: main window
116: subwindow
117: blood vessel change index display portion
122: shape
123: surface layer blood vessel
124: middle deep layer blood vessel
132: second blood vessel image
203: determination unit
208: determination result
217: determination result display portion
310: endoscope system
403: third endoscope image
408: blood vessel change index
408a, 408b: blood vessel change index
411: first region of interest
412: second region of interest
413: third region of interest
414: main window
415: first subwindow
416: second subwindow
417: blood vessel change index display portion
501: calculation start button
511: first blood vessel parameter display portion
512: second blood vessel parameter display portion
600: capsule endoscope
602: light source
603: light source control unit
604: imaging sensor
606: image signal acquisition processing unit
608: transmitting and receiving antenna
P1: first blood vessel parameter
P2: second blood vessel parameter
P3: third blood vessel parameter
Q1: first blood vessel parameter
Q2: second blood vessel parameter
Rc: change rate
Rm: magnification
T1: imaging time
T2: imaging time
T3: imaging time
TH1: first threshold value
TH2: second threshold value

What is claimed is:

1. An image processing apparatus, comprising:
a processor and a memory comprising instructions to be executed by the processor, wherein the processor is configured to execute:
an image acquisition unit that acquires a plurality of endoscope images obtained by imaging an observation target at different times with an endoscope;
a blood vessel extraction unit that extracts blood vessels of the observation target from the plurality of endoscope images;
a blood vessel information calculation unit that calculates a plurality of pieces of blood vessel information in a plurality of units of measurement for each of the blood vessels extracted from the endoscope images;
a blood vessel parameter calculation unit that calculates a blood vessel parameter, which is relevant to the blood vessel extracted from each of the endoscope images, by calculation using the blood vessel information in the plurality of units of measurements, wherein the blood vessel parameter is a weighted sum of the pieces of blood vessel information; and
a blood vessel change index calculation unit that calculates a blood vessel change index, which indicates a temporal change of the blood vessel of the observation target, using the blood vessel parameter.

2. The image processing apparatus according to claim 1, wherein the blood vessel information is the number of blood vessels, a thickness, a change in thickness, complexity of thickness change, a length, a change in length, the number of branches, a branching angle, a distance between branch points, the number of crossings, an inclination, an area, a density, a depth with respect to a mucous membrane as a reference, a height difference, an interval, a contrast, a color, a color change, a degree of meandering, blood concentration, oxygen saturation, a proportion of arteries, a proportion of veins, concentration of administered coloring agent, a running pattern, or a blood flow rate.

3. The image processing apparatus according to claim 1, wherein the blood vessel change index is a difference between the blood vessel parameters or a magnification or change rate of the blood vessel parameter.

4. The image processing apparatus according to claim 1, wherein the blood vessel information calculation unit calculates the blood vessel information for a region of interest set in a part or entirety of the endoscope image.

5. The image processing apparatus according to claim 4, wherein the blood vessel information is a statistic in the region of interest.

6. The image processing apparatus according to claim 1, wherein the blood vessel change index calculation unit calculates the blood vessel change index inductively in order of imaging times of the endoscope images.

7. The image processing apparatus according to claim 1, wherein the blood vessel change index calculation unit calculates the blood vessel change index by setting one of imaging times of the endoscope images as a reference time.

8. An endoscope system, comprising:
an endoscope that images an observation target; and
an image processing apparatus, comprising: a processor and a memory comprising instructions to be executed by the processor, wherein the processor is configured to execute:
an image acquisition unit that acquires a plurality of endoscope images obtained by imaging the observation target at different times with the endoscope;
a blood vessel extraction unit that extracts blood vessels of the observation target from the plurality of endoscope images;
a blood vessel information calculation unit that calculates a plurality of pieces of blood vessel information in a plurality of units of measurement for each of the blood vessels extracted from the endoscope images;
a blood vessel parameter calculation unit that calculates a blood vessel parameter, which is relevant to the blood vessel extracted from each of the endoscope images, by calculation using the blood vessel information in the plurality of units of measurements, wherein the blood vessel parameter is a weighted sum of the pieces of blood vessel information; and
a blood vessel change index calculation unit that calculates a blood vessel change index, which indicates a temporal change of the blood vessel of the observation target, using the blood vessel parameter.

9. An image processing method, comprising:
- acquiring a plurality of endoscope images obtained by imaging an observation target at different times with an endoscope;
- extracting blood vessels of the observation target from the plurality of endoscope images;
- calculating a plurality of pieces of blood vessel information in a plurality of units of measurement for each of the blood vessels extracted from the endoscope images;
- calculating a blood vessel parameter, which is relevant to the blood vessel extracted from each of the endoscope images, by calculation using the blood vessel information in the plurality of units of measurements, wherein the blood vessel parameter is a weighted sum of the pieces of blood vessel information; and
- calculating a blood vessel change index, which indicates a temporal change of the blood vessel of the observation target, using the blood vessel parameter.

10. The image processing apparatus according to claim 1, wherein each piece of blood vessel information is a physical value of a blood vessel with a unit of measurement.

11. The image processing apparatus according to claim 1, wherein the blood vessel change index calculation unit calculates the blood vessel change index by setting an imaging time of a first endoscope image as a reference time, and calculates a blood vessel change index as a difference between a second blood vessel parameter from a second endoscope image at an imaging time of the second endoscope image with respect to a first blood vessel parameter from the first endoscope image at the reference time.

* * * * *